US009555167B2

(12) United States Patent
Schmid et al.

(10) Patent No.: US 9,555,167 B2
(45) Date of Patent: Jan. 31, 2017

(54) BIOCOMPATIBLE ANTIMICROBIAL COMPOSITIONS

(75) Inventors: Matthew J. Schmid, Roberts, WI (US); Ronald W. Ausen, St. Paul, MN (US); Jay M. Jennen, Forest Lake, MN (US); Kelly S. Anderson, Houlton, WI (US); Matthew T. Scholz, Woodbury, MN (US); Robert W. Peterson, Spring Valley, WI (US); Erin A. Satterwhite, Chatham, NJ (US); Francis E. Porbeni, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 729 days.

(21) Appl. No.: 11/609,237

(22) Filed: Dec. 11, 2006

(65) Prior Publication Data
US 2008/0142023 A1 Jun. 19, 2008

(51) Int. Cl.
*A61L 31/16* (2006.01)
*A01N 25/10* (2006.01)
*A61L 29/06* (2006.01)
*A61L 29/16* (2006.01)
*A61L 31/06* (2006.01)
*A01N 25/30* (2006.01)
*A61B 17/00* (2006.01)

(52) U.S. Cl.
CPC ............ *A61L 31/16* (2013.01); *A01N 25/10* (2013.01); *A61B 46/00* (2016.02); *A61L 29/06* (2013.01); *A61L 29/16* (2013.01); *A61L 31/06* (2013.01); *A61B 2017/00889* (2013.01); *A61L 2300/404* (2013.01)

(58) Field of Classification Search
CPC .................. A61F 13/15252; A61F 2013/8414
USPC .... 424/1.11, 1.41, 1.49, 133.1, 141.1, 158.1, 424/178.1, 400, 401, 422, 423, 426, 427, 424/434, 436, 443, 448, 449, 450, 456, 424/457; 514/1, 11, 12, 108, 149, 152, 514/159, 162, 169, 171, 172, 173, 176, 514/177, 178, 18, 215
See application file for complete search history.

(56) References Cited

U.S. PATENT DOCUMENTS

| | | | |
|---|---|---|---|
| 2,561,010 A * | 7/1951 | Carson ........................ 206/524.6 |
| 3,389,827 A | 6/1968 | Abere et al. | |
| 3,565,985 A | 2/1971 | Schrenk et al. | |
| 4,122,213 A | 10/1978 | Ito et al. | |
| 4,310,509 A | 1/1982 | Berglund et al. | |
| 4,323,557 A | 4/1982 | Rosso et al. | |
| 4,348,455 A * | 9/1982 | Clayton ........................ 428/336 |
| 4,624,679 A | 11/1986 | McEntee | |
| 4,737,410 A | 4/1988 | Kantner | |
| 4,744,365 A | 5/1988 | Kaplan et al. | |
| 5,208,257 A | 5/1993 | Kabara | |
| 5,236,427 A | 8/1993 | Hamajima | |
| 5,268,733 A | 12/1993 | Wright et al. | |
| 5,278,256 A * | 1/1994 | Bellis ........................... 525/450 |
| 5,326,572 A | 7/1994 | Mehra et al. | |
| 5,427,842 A | 6/1995 | Bland et al. | |
| 5,475,063 A | 12/1995 | Kaplan et al. | |
| 5,480,394 A | 1/1996 | Ishikawa | |
| 5,525,646 A * | 6/1996 | Lundgren ............... A61L 27/18 424/423 |
| 5,545,485 A | 8/1996 | Hashitani et al. | |
| 5,569,461 A * | 10/1996 | Andrews ....................... 424/405 |
| 5,589,122 A | 12/1996 | Leonard et al. | |
| 5,599,602 A | 2/1997 | Leonard et al. | |
| 5,607,686 A * | 3/1997 | Totakura et al. ............. 424/426 |
| 5,639,466 A | 6/1997 | Ford et al. | |
| 5,660,922 A | 8/1997 | Herridge et al. | |
| 5,665,776 A | 9/1997 | Yu et al. | |
| 5,723,004 A * | 3/1998 | Dereume et al. ............ 623/1.35 |
| 5,744,516 A | 4/1998 | Hashitani et al. | |
| 5,883,199 A | 3/1999 | McCarthy et al. | |
| 5,912,372 A | 6/1999 | Mazer et al. | |
| 5,952,433 A | 9/1999 | Wang et al. | |
| 5,981,038 A | 11/1999 | Weimer et al. | |
| 5,997,568 A | 12/1999 | Liu | |
| 6,075,118 A | 6/2000 | Wang et al. | |
| 6,077,931 A | 6/2000 | Noda | |
| 6,093,792 A | 7/2000 | Gross et al. | |
| 6,111,060 A | 8/2000 | Gruber et al. | |
| 6,117,928 A | 9/2000 | Hiltunen et al. | |
| 6,143,863 A | 11/2000 | Gruber et al. | |
| 6,248,363 B1 * | 6/2001 | Patel et al. .................... 424/497 |
| 6,417,294 B1 | 7/2002 | Obuchi et al. | |
| 6,482,341 B1 | 11/2002 | Jongboom et al. | |
| 6,605,069 B1 | 8/2003 | Albers et al. | |

(Continued)

FOREIGN PATENT DOCUMENTS

DE 4400770 C1 * 2/1995 ............ A61L 15/44
EP 1 041 105 A2 10/2000

(Continued)

OTHER PUBLICATIONS

"Properties and uses of common formulation lipids, surfactants and cosolvents", Pouton, http://www.aapspharmaceutica.com/meetings/files/85/03/poultona.pdf.*

(Continued)

*Primary Examiner* — Mark V Stevens

(57) ABSTRACT

Antimicrobial compositions comprising aliphatic polyester, and an antimicrobial component effective for antimicrobial activity, and, in some embodiments, an enhancer. Example: blend of poly(lactic acid) polymer (55g) with propyleneglycol monolaurate antimicrobial component (9g), and benzoic acid enhancer (1g). Inventive resin compositions are effective against gram negative and gram positive bacteria, mold and mildew. Preferred compositions comprise materials that are GRAS (Generally Regarded As Safe).

38 Claims, No Drawings

(56) References Cited

U.S. PATENT DOCUMENTS

| | | | |
|---|---|---|---|
| 6,645,618 B2 | 11/2003 | Hobbs et al. | |
| 6,689,608 B1 * | 2/2004 | Mikos | A61F 2/18 424/426 |
| 6,756,428 B2 | 6/2004 | Denesuk | |
| 6,762,339 B1 * | 7/2004 | Klun et al. | 602/58 |
| 7,049,057 B2 | 5/2006 | Atala et al. | |
| 8,721,943 B2 | 5/2014 | Moore et al. | |
| 8,802,002 B2 | 8/2014 | Berrigan et al. | |
| 8,858,986 B2 | 10/2014 | Scholz et al. | |
| 8,932,704 B2 | 1/2015 | Porbeni et al. | |
| 2001/0051277 A1 * | 12/2001 | Van Antwerp et al. | 428/457 |
| 2003/0027833 A1 * | 2/2003 | Cleary et al. | 514/270 |
| 2003/0143415 A1 * | 7/2003 | Seta et al. | 428/523 |
| 2004/0024141 A1 | 2/2004 | Hasebe et al. | |
| 2004/0024374 A1 | 2/2004 | Hjorth | |
| 2004/0033913 A1 * | 2/2004 | Dahms et al. | 510/119 |
| 2004/0086667 A1 * | 5/2004 | Iriya et al. | 428/34.1 |
| 2004/0241216 A1 | 12/2004 | Klun et al. | |
| 2005/0084471 A1 * | 4/2005 | Andrews | A01N 37/12 424/70.31 |
| 2005/0089539 A1 * | 4/2005 | Scholz et al. | 424/401 |
| 2005/0242466 A1 * | 11/2005 | Kanazawa et al. | 264/236 |
| 2006/0013857 A1 | 1/2006 | Kronenthal | |
| 2006/0051384 A1 | 3/2006 | Scholz et al. | |
| 2006/0091576 A1 | 5/2006 | Takase | |
| 2006/0099237 A1 * | 5/2006 | Modak et al. | 424/422 |
| 2006/0246149 A1 | 11/2006 | Buchholz et al. | |
| 2006/0275349 A1 * | 12/2006 | Andrews et al. | 424/443 |
| 2006/0282052 A1 | 12/2006 | Saito | |
| 2007/0082573 A1 | 4/2007 | Noda | |
| 2007/0166438 A1 | 7/2007 | Kitahata et al. | |
| 2010/0210756 A1 * | 8/2010 | Takenaka et al. | 523/124 |
| 2011/0151737 A1 | 6/2011 | Moore et al. | |
| 2011/0189463 A1 | 8/2011 | Moore et al. | |
| 2012/0077886 A1 | 3/2012 | Scholz et al. | |
| 2012/0088424 A1 | 4/2012 | Eric et al. | |
| 2013/0288556 A1 | 10/2013 | Moore et al. | |
| 2014/0210141 A1 | 7/2014 | Moore et al. | |
| 2015/0004866 A1 | 1/2015 | Scholz et al. | |

FOREIGN PATENT DOCUMENTS

| | | |
|---|---|---|
| JP | 10-036650 | 2/1998 |
| JP | 2000-280410 | 10/2000 |
| JP | 2004-36091 | 12/2004 |
| JP | 2005-179607 | 7/2005 |
| WO | WO 84/04311 | 11/1984 |
| WO | WO 94/07941 | 4/1994 |
| WO | WO 94/07949 | 4/1994 |
| WO | WO 96/22330 | 7/1996 |
| WO | WO 98/24951 | 6/1998 |
| WO | WO 98/50611 | 11/1998 |
| WO | WO 99/06456 | 2/1999 |
| WO | WO 99/50345 | 10/1999 |
| WO | WO 00/12606 | 3/2000 |
| WO | WO 00/28815 | 5/2000 |
| WO | WO 00/71183 A1 | 11/2000 |
| WO | WO 0071183 A1 * | 11/2000 |
| WO | WO 01/94292 A1 | 12/2001 |
| WO | WO 02/087328 A2 | 11/2002 |
| WO | WO 03/013454 A1 | 2/2003 |
| WO | WO 03/034842 A1 | 5/2003 |
| WO | WO 2004/045663 A1 | 6/2004 |
| WO | WO 2004045663 A1 * | 6/2004 |
| WO | WO 2004/092283 | 10/2004 |
| WO | WO 2004093794 A2 * | 11/2004 |
| WO | WO 2006/042364 A1 | 4/2006 |
| WO | WO 2014/059239 A1 | 4/2014 |

OTHER PUBLICATIONS

"Properties and uses of common formulation lipids, surfactants and cosolvents", Pouton, http://www.aapspharmaceutic.com/meetings/files/85/poultona.pdf.*

"Characterization of a homologous series of D,L-lactic acid oligomers; a mechanistic study on the degradation kinetics in vitro", Schliecker et al., Biomaterials, 24, (2003), 3835-3844.*

Martin et al (Preparation and Behavior of Acetyl Monoglycerides, 1972, Journal of the American Oil Chemists' Society, vol. 49, pp. 683-687).*

Lambert et al. (The synergistic effect of EDTA/antimicrobial combinations on Pseudomonas aeruginosa, 2004, Journal of Applied Microbiology, vol. 96, pp. 244-253).*

The Good Scents Company (Ethyl hexyl glycerin information, http://www.thegoodscentscompany.com/data/rw1361601.html, 2014).*

Amresco (New Chelating Agent Offerings, http://www.amresco-inc.com/new-chelating-agents.cmsx, 2014).*

Katti et al (Journal of Biomedical Materials Research, 2004, pp. 286-296).*

Schlievert et al (Plos One, 2012, vol. 7, e40350).*

"Antibacterial Finishes on Textile Materials: Assessment of," AATCC Technical Manual, 1997, pp. 143-144.

ISA210 International Search Report, Application No. PCT/US2009/039375.

Non-final Office Action in U.S. Appl. No. 12/098,517, mailed Nov. 18, 2013, 14 pages.

U.S. Appl. No. 62/069,934, filed Oct. 29, 2014, Chakravarty et al.

Donnelly, "Stability of Cefazolin Sodium in Polypropylene Syringes and Polyvinylchloride Minibags," *The Canadian Journal of Hospital Pharmacy*, 2011;64(4):241-245.

Kodym et al., "Physical and Chemical Properties and Stability of Sodium Cefazolin in Buffered Eye Drops Determined with HPLC Method," *Acta Poloniae Pharmaceutica-Drug Research*, 2012;69(1):95-105.

* cited by examiner

BIOCOMPATIBLE ANTIMICROBIAL COMPOSITIONS

TECHNICAL FIELD

The present invention relates to antimicrobial compositions.

BACKGROUND

The use of biodegradable polymers has been described to reduce the amount of waste materials land-filled and the number of disposal sites. Biodegradable materials have adequate properties to permit them to break down when exposed to conditions which lead to composting. Examples of materials thought to be biodegradable include aliphatic polyesters such as poly (lactic acid), poly(glycolic acid), poly(caprolactone), copolymers of lactide and glycolide, poly(ethylene succinate), and combinations thereof.

Degradation of aliphatic polyesters can occur through multiple mechanisms including hydrolysis, transesterification, chain scission, and the like. Instability of such polymers during processing can occur at elevated temperatures as described in WO 94/07941 (Gruber et. al.).

The processing of aliphatic polyesters as microfibers has been described in U.S. Pat. No. 6,645,618. U.S. Pat. No. 6,111,160 (Gruber et.al.) discloses the use of melt stable polylactides to form nonwoven articles via melt blown and spunbound processes.

Antimicrobial agents (e.g. antibiotics, antiseptics including antiviral, antifungal and antibacterial agents) play an important part in current medical therapy. This is particularly important in the fields of dermatology as well as skin and wound antisepsis. U.S. Patent Application Publication 2005/0089539 (Scholz et.al.) is herein incorporated by reference.

Antimicrobial polymer compositions are known, as exemplified by U.S. Pat. Nos. 5,639,466 (Ford et. al.) and U.S. Pat. No. 6,756,428 (Denesuk). The addition of antimicrobial agents to hydrophilic polypropylene fibers having antimicrobial activity has been described in U.S. Patent Application Publication No. 2004/0241216 (Klun et.al.). These fibrous materials include nonwovens, wovens, knit webs, and knit batts.

The synergistic effect of antimicrobial agents, such as fatty acid monoesters, and enhancers have been described in WO 00/71183 (Andrews et. al.), incorporated herein by reference.

DISCLOSURE OF INVENTION

The present disclosure is directed to a composition, article and method for making an antimicrobial (preferably biocompatible) composition. The inventive compositions may be melt-processable and have utility in a variety of food safety, medical and water purification applications. In one aspect, the composition comprises a thermoplastic aliphatic polyester; an antimicrobial component incorporated within the polyester, in which the antimicrobial component is present at greater than 1 percent by weight of the aliphatic polyester; and an enhancer. The aliphatic polyester is in sufficient proportion to the antimicrobial component to yield an effective antimicrobial composition. The antimicrobial component is selected from cationic antimicrobial amine compounds (preferably present in amounts greater than 5 weight percent of the aliphatic polyester), fatty acid esters of polyhydric alcohols, fatty ethers of polyhydric alcohols, hydroxy acid esters of fatty alcohols, alkoxylated derivatives thereof (having less than 5 moles of alkoxide group per mole of polyhydric alcohol) and combinations thereof. The enhancer provides for enhanced antimicrobial activity of the antimicrobial component in the composition.

In another aspect, the compositions of this disclosure are biocompatible. The composition comprises components which are biodegradable and listed GRAS (Generally Regarded As Safe), direct food additives or food processing aids by the United States Food and Drug Administration (FDA).

In some embodiments, the inventive compositions do not require an enhancer. In preferred compositions, the antimicrobial component is greater than 5 weight percent, more preferably greater than 13% of the aliphatic polyester, and octoxyglycerin is excluded from the selection of antimicrobial components. The antimicrobial component is selected from cationic antimicrobial amine compounds, saturated or unsaturated fatty ethers of polyhydric alcohols, hydroxy acid esters of alcohols; alkoxylated derivatives thereof and combinations thereof.

Exemplary aliphatic polyesters are poly (lactic acid), poly (glycolic acid), poly(lactic-co-glycolic acid), blends, and copolymers thereof.

The antimicrobial component may be selected from $C_1$-$C_{14}$ propylene monoesters, and glycerol monoesters. Examples are propylene glycol monolaurate, propylene glycol monocaprylate, glycerol monolaurate, and combinations thereof.

Inventive articles comprise molded polymeric articles, polymeric sheet, polymeric fibers, woven webs, nonwoven webs, porous membranes, polymeric foams, thermal or adhesive laminates, layered compositions, and combinations thereof made of the compositions described above. Examples of useful articles of this disclosure are wound contact materials made of a film, foam and/or woven or nonwoven comprising the inventive composition and surgical drapes or surgical gowns made of the inventive composition.

The method of the present disclosure comprises providing the aliphatic polyester and the antimicrobial component as described, and the enhancer for those embodiments that include it, and mixing these materials sufficiently to yield a biocompatible antimicrobial composition.

In one aspect, the polymer composition is melt processable, such that the polymer is capable of being extruded.

In another aspect, the polymer is solvent soluble or dispersible and the composition may be solvent cast, solvent spun to form films or fibers, or foamed.

The melt processable composition of aliphatic polyesters and antimicrobial components (which can plasticize the polyester) are biocompatible and exhibit antimicrobial activity. The plasticized aliphatic polyester generally has a lower melt processing temperature and can yield a more flexible output material. Materials such as lactic acid, and the fatty acid monoesters presented are recognized as GRAS.

Desirably, antimicrobial components migrate to the surface, and may be released into the surrounding polymer matrix or medium in which microbe growth is to be controlled. In the inventive compositions, the antimicrobial components are released as the aliphatic polyester degrades and/or swells, giving them, in some measure, a self-disinfecting property. The degradation of the aliphatic polyester may be controlled to adjust the release characteristics of the antimicrobial component. The antimicrobial component may migrate through the polymer. The enhancer, either added separately, or possibly generated during the degradation of the aliphatic polyester, improves the biocidal activity of the antimicrobial component. The degradation of the aliphatic polyester of the composition may renew the surface of an article comprised of the inventive composition, possibly reducing surface fouling and biofilm formation.

The antimicrobial component may be biodegradable. It may decompose by hydrolysis, transesterification, or by the action of bacteria and/or bacterial enzymes. The entire composition may degrade into environmentally acceptable components. In some embodiments, the antimicrobial component may be resistant to degradation or not degrade appreciably during the useful life of articles made of the inventive composition. Mixtures of biodegradable and non-degradable antimicrobial components may be used.

Preferred embodiments of the inventive resin compositions have both a controlled release characteristic, and are biocompatible.

DETAILED DESCRIPTION

For the following defined terms, these definitions shall be applied, unless a different definition is given in the claims or elsewhere in the specification.

The term "antimicrobial" or "antimicrobial activity" means having sufficient antimicrobial activity to kill pathogenic and non-pathogenic microorganisms including bacteria, fungi, algae and virus. Preferred antimicrobial materials exhibit at least 1 log reduction, preferably 2 log reduction, and most preferably 4 log reduction of S. aureus (AATC 25923) in 60 minutes from an initial inoculum of $1-3\times10^7$ cfu/ml when tested in Mueller Hinton broth at 35° C. at a concentration of 0.25 wt. % in a Rate of Kill assay using an appropriate neutralizer as described in G. Nicoletti, V. Boghossian, F. Gurevitch, R. Borland and P. Mogenroth, "The Antimicrobial Activity in Vitro of Chlorhexidine, a Mixture of Isothiazolinones (Kathon CG) and Cetyl Trimethyl Ammonium Bromide (CTAB)", *Journal of Hospital Infection*, vol. 23, pp. 87-111, (1993).

The term "biodegradable" means degradable by the action of naturally occurring microorganisms such as bacteria, fungi and algae and/or natural environmental factors such as hydrolysis, transesterification, exposure to ultraviolet or visible light (photodegradable) and enzymatic mechanisms or combinations thereof.

The term "biocompatible" means biologically compatible by not producing toxic, injurious or immunological response in living tissue. Biocompatible materials may also be broken down by biochemical and/or hydrolytic processes and absorbed by living tissue. Test methods used include ASTM F719 for applications where the compositions contact tissue such as skin, wounds, mucosal tissue including in an orifice such as the esophagus or urethra, and ASTM F763 for applications where the compositions are implanted/in tissue.

The term "sufficient amount" or "effective amount" means the amount of the antimicrobial component and/or enhancer when in a composition, as a whole, provides an antimicrobial (including, for example, antiviral, antibacterial, or antifungal) activity that reduces, prevents growth of, or eliminates colony forming units for one or more species of microorganisms such that an acceptable level of the organism results. Typically, this is a level low enough not to cause clinical symptoms on tissue or to result in spreading microbes from one hard surface to another in sufficient; quantity to cause disease, and is desirably a non-detectable level. The concentrations or amounts of the components, when considered separately, may not kill to an acceptable level, may not kill as broad a spectrum of undesired microorganisms, or may not kill as fast; however, when used together such components provide an enhanced antimicrobial activity (as compared to the same components used alone under the same conditions). Measurable antimicrobial activity is further described in American Association of Textile and Color Chemists (AATCC) Test Method 100-2004 (AATCC Technical manual, Vol. 80, 2005, pp. 149-151) and Japanese Industrial Standard (JIS) Z2801:2000 (Japanese Standards Association, 2001, pp. 1-11).

The term "enhancer" means a component that enhances the effectiveness of the antimicrobial component such that when the composition without the enhancer is used separately, it does not provide the same level of antimicrobial activity as the composition including enhancer. An enhancer in the absence of the antimicrobial component may not provide any appreciable antimicrobial activity. The enhancing effect can be with respect to the level of kill, the speed of kill, and/or the spectrum of microorganisms killed, and may not be seen for all microorganisms. In fact, an enhanced level of kill is most often seen in Gram negative bacteria such as *Escherichia coli*. An enhancer may be a synergist such that when combined with the remainder of the composition, the combined antimicrobial activity is greater than the sum of the activity of the composition without the enhancer component and the composition without the antimicrobial component.

The term "antimicrobial component" means an antiseptic that generally is a small molecule having a molecular weight less than about 1000 Daltons, and often less than 500, daltons capable of killing at least one species of bacteria, fungi, and/or virus or having antimicrobial activity. Preferred antimicrobial components are lipophilic preferably having a solubility in water of no greater than 1.0 gram per 100 grams (1.0 g/100 g) deionized water. For prolonged use applications, preferred antimicrobial components or antimicrobial lipids have a solubility in water of no greater than 0.5 g/100 g deionized water, more preferably, no greater than 0.25 g/100 g deionized water, and even more preferably, no greater than 0.10 g/100 g deionized water. Solubilities are described using radio-labeled compounds as described under "Conventional Solubility Estimations" in Solubility of Long-Chain Fatty Acids in Phosphate Buffer at ph 7.4, Henrik vorum et.al., in *Biochimica et. Biophysica Acta.*, 1126, 135-142(1992). Preferred antimicrobial components have a solubility in deionized water of at least 100 micrograms (μg) per 100 grams deionized water, more preferably, at least 500 μg/100 μg deionized water, and even more preferably, at least 1000 μg/100 g deionized water.

The term "fatty" means a straight or branched chain alkyl or alkylene moiety having 6 to 22 (odd or even number) carbon atoms, unless otherwise specified.

The recitation of numerical ranges by endpoints includes all numbers subsumed within that range (e.g. 1 to 5 includes 1, 1.5, 2, 2.75, 3, 3.8, 4, and 5).

As used in this specification and the appended claims, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities or ingredients, measurement of properties and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques.

Aliphatic polyesters useful in the present invention include homo- and copolymers of poly(hydroxyalkanoates) and homo- and copolymers of those aliphatic polyesters derived from the reaction product of one or more polyols with one or more polycarboxylic acids and is typically formed from the reaction product of one or more alkanediols with one or more alkanecarboxylic acids (or acyl derivatives). Polyesters may further be derived from multifunctional polyols, e.g. glycerin, sorbitol, pentaerythritol, and combinations thereof, to form branched, star, and graft homo- and copolymers. Miscible and immiscible blends of aliphatic polyesters with one or more additional semicrystalline or amorphous polymers may also be used.

One useful class of aliphatic polyesters are poly(hydroxyalkanoates)j derived by condensation or ring-opening polymerization of hydroxy acids, or derivatives thereof. Suitable poly(hydroxyalkanoates) may be represented by the formula:

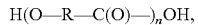

H(O—R—C(O)—)$_n$OH, where R is an alkylene moiety that may be linear or branched having 1 to 20 carbon atoms, preferably 1 to 12 carbon atoms optionally substituted by catenary (bonded to carbon atoms in a carbon chain) oxygen atoms; n is a number such that the ester is polymeric, and is preferably a number such that the molecular weight of the aliphatic polyester is at least 10,000, preferably at least 30,000, and most preferably at least 50,000 daltons. Although higher molecular weight polymers generally yield films with better mechanical properties, for both melt processed and solvent cast polymers excessive viscosity is undesirable. It is a significant advantage of the present invention that the antimicrobial component in many embodiments plasticizes the polyester component allowing for melt processing and solvent casting of higher molecular weight polymers. Thus, the molecular weight of the aliphatic polyester is typically less than 1,000,000, preferably less than 500,000, and most preferably less than 300,000 daltons, R may further comprise one or more catenary (i.e. in chain) ether oxygen atoms. Generally, the R group of the hydroxy acid is such that the pendant hydroxyl group is a primary or secondary hydroxyl group.

Useful poly(hydroxyalkanoates) include, for example, homo- and copolymers of poly(3-hydroxybutyrate), poly(4-hydroxybutyrate), poly(3-hydroxyvalerate), poly(lactic acid) (as known as polylactide), poly(3-hydroxypropanoate), poly(4-hydropentanoate), poly(3-hydroxypentanoate), poly(3-hydroxyhexanoate), poly(3-hydroxyheptanoate), poly(3-hydroxyoctanoate), polydioxanone, polycaprolactone, and polyglycolic acid (i.e. polyglycolide). Copolymers of two or more of the above hydroxy acids may also be used, for example, poly(3-hydroxybutyrate-co-3-hydroxyvalerate), poly(lactate-co-3-hydroxypropanoate), poly(glycolide-co-p-dioxanone), and poly(lactic acid-co-glycolic acid). Blends of two or more of the poly(hydroxyalkanoates) may also be used, as well as blends with one or more semicrystalline or amorphous polymers and/or copolymers.

The aliphatic polyester may be a block copolymer of poly(lactic acid-co-glycolic acid). Aliphatic polyesters useful in the inventive compositions may include homopolymers, random copolymers, block copolymers, star-branched random copolymers, star-branched block copolymers, dendritic copolymers, hyperbranched copolymers, graft copolymers, and combinations thereof.

Another useful class of aliphatic polyesters includes those aliphatic polyesters derived from the reaction product of one or more alkanediols with one or more alkanedicarboxylic acids (or acyl derivatives). Such polyesters have the general formula:

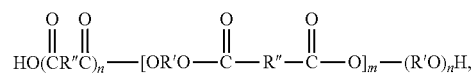

$$HO(CR''C)_n\text{—}[OR'O\text{—}\overset{O}{\overset{\|}{C}}\text{—}R''\text{—}\overset{O}{\overset{\|}{C}}\text{—}O]_m\text{—}(R'O)_nH,$$

where R' and R" each represent an alkylene moiety that may be linear or branched having from 1 to 20 carbon atoms, preferably 1 to 12 carbon atoms, and m is a number such that the ester is polymeric, and is preferably a number such that the molecular weight of the aliphatic polyester is at least 10,000, preferably at least 30,000, and most preferably at least 50,000 daltons, but less than 1,000,000, preferably less than 500,000 and most preferably less than 300,000 daltons. Each n is independently 0 or 1. R' and R" may further comprise one or more catenary (i.e. in chain) ether oxygen atoms.

Examples of aliphatic polyesters include those homo-and copolymers derived from (a) one or more of the following diacids (or derivative thereof): succinic acid, adipic acid, 1,12dicarboxydodecane, fumaric acid, glutaric acid, diglycolic acid, and maleic acid; and (b) one or more of the following diols: ethylene glycol, polyethylene glycol, 1,2-propane diol, 1,3-propanediol, 1,2-propanediol, 1,2-butanediol, 1,3-butanediol, 1,4-butanediol, 2,3-butanediol, 1,6-hexanediol, 1,2 alkane diols having 5 to 12 carbon atoms, diethylene glycol, polyethylene glycols having a molecular weight of 300 to 10,000 daltons, preferably 400 to 8,000 daltons, propylene glycols having a molecular weight of 300 to 4000 daltons, block or random copolymers derived from ethylene oxide, propylene oxide, or butylene oxide, dipropylene glycol and polypropylene glycol, and (c) optionally a small amount, i.e. 0.5-7.0 mole % of a polyol with a functionality greater than two such as glycerol, neopentyl glycol, and pentaerythritol.

Such polymers may include polybutylenesuccinate homopolymer, polybutylene adipate homopolymer, polybutyleneadipate-succinate copolymer, polyethylenesuccinate-adipate copolymer, polyethylene glycol succinate and polyethylene adipate homopolymer.

Commercially available aliphatic polyesters include poly (lactide); poly(glycolide), poly(lactide-co-glycolide), poly (L-lactide-co-trimethylene carbonate), poly(dioxanone), poly(butylene succinate), and poly(butylene adipate).

Useful aliphatic polyesters include those derived from semicrystalline polylactic acid. Poly(lactic acid) or polylactide has lactic acid as its principle degradation product, which is commonly found in nature, is non-toxic and is widely used in the food, pharmaceutical and medical industries. The polymer may be prepared by ring-opening polymerization of the lactic acid dimer, lactide. Lactic acid is optically active and the dimer appears in four different forms: L,L-lactide, D,D-lactide, D,L-lactide (meso lactide) and a racemic mixture of L,L- and D,D-. By polymerizing these lactides as pure compounds or as blends, poly(lactide)

polymers may be obtained having different stereochemistries and different physical properties, including crystallinity. The L,L- or D,D-lactide yields semicrystalline poly (lactide), while the poly(lactide) derived from the D,L-lactide is amorphous.

The polylactide preferably has a high enantiomeric ratio to maximize the intrinsic crystallinity of the polymer. The degree of crystallinity of a poly(lactic acid) is based on the regularity of the polymer backbone and the ability to crystallize with other polymer chains. If relatively small amounts of one enantiomer (such as D-) is copolymerized with the opposite enantiomer (such as L-) the polymer chain becomes irregularly shaped, and becomes less crystalline. For these reasons, when crystallinity is favored, it is desirable to have a poly(lactic acid) that is at least 85% of one isomer, at least 90%, or at least 95% in order to maximize the crystallinity.

An approximately equimolar blend of D-polylactide and L-polylactide is also useful. This blend forms a unique crystal structure having a higher melting point (~210° C.) than does either the D-poly(lactide) and L-(polylactide) alone (~190° C.), and has improved thermal stability, see H. Tsujiet. al., *Polymer,* 40 (1999) 6699-6708.

Copolymers, including block and random copolymers, of poly(lactic acid) with other aliphatic polyesters may also be used. Useful co-monomers include glycolide, beta-propiolactone, tetramethylglycolide, beta-butyrolactone, gamma-butyrolactone, pivalolactone, 2-hydroxybutyric acid, alpha-hydroxyisobutyric acid; alpha-hydroxyvaleric acid, alpha-hydroxyisovaleric acid, alpha-hydroxycaproic acid, alpha-hydroxyethylbutyric acid, alpha-hydroxyisocaproic acid, alpha-hydroxy-beta-methylvaleric acid, alpha-hydroxyoctanoic acid, alpha-hydroxydecanoic acid, alpha-hydroxymyristic acid, and alpha-hydroxystearic acid.

Blends of poly(lactic acid) and one or more other aliphatic polyesters, or one or more other polymers may also be used. Examples of useful blends include poly(lactic acid) and poly(vinyl alcohol), polyethylene glycol/polysuccinate, polyethylene oxide, polycaprolactone and polyglycolide.

Poly(lactide)s may be prepared as described in U.S. Pat. No. 6,111,060 (Gruber, et al.), U.S. Pat. No. 5,997,568 (Liu), U.S. Pat. No. 4,744,365 (Kaplan et al.), U.S. Pat. No. 5,475,063 (Kaplan et al.), U.S. Pat. No. 6,143,863 (Gruber et al.), U.S. Pat. No. 6,093,792 (Gross et al), U.S. Pat. No. 6,075,118 (Wang et al), and U.S. Pat. No. 5,952,433 (Wang et al.), WO 98/24951 (Tsai et al.), WO 00/12606 (Tsai et al.), WO 84/04311 (Lin), U.S. Pat. No. 6,117,928 (Hiltunen et al.), U.S. Pat. No. 5,883,199 (McCarthy et al.), WO 99/50345 (Kolstad et al.), WO 99/06456 (Wang et al.), WO 94/07949 (Gruber et al.), WO 96/22330 (Randall et al.), and WO 98/50611 (Ryan et al.), the disclosure of each U.S. patent incorporated herein by reference. Reference may also be made to J. W. Leenslag, et al., *J. Appl. Polymer Science,* vol. 29 (1984), pp 2829-2842, and H. R. Kricheldorf, *Chemosphere. vol.* 43, (2001) 49-54.

The molecular weight of the polymer should be chosen so that the polymer may be processed as a melt or cast from a solvent. For polylactide, for example, the molecular weight may be from about 10,000 to 1,000,000 daltons, and is preferably from about 30,000 to 300,000 daltons. By "melt-processible", it is meant that the aliphatic polyesters are fluid or can be pumped or extruded at the temperatures used to process the articles (e;g. films), and do not degrade or gel at those temperatures to the extent that the physical properties are so poor as to be unusable for the intended application. Thus, many of the inventive materials may be made into films by extrusion, casting, thermal pressing, and the like.

They can be made into nonwovens using melt processes such as spun bond, blown microfiber, melt spinning and the like. Certain embodiments also may be injection molded. Generally, weight average molecular weight ($M_w$) of the polymers is above the entanglement molecular weight, as determined by a log-log plot of viscosity versus number average molecular weight ($M_n$). Above the entanglement molecular weight, the slope of the plot is about 3.4, whereas the slope of lower molecular weight polymers is 1.

The aliphatic polyester of the antimicrobial composition of this disclosure typically comprises at least 50 weight percent, preferably at least 60 weight percent, and most preferably at least 65 weight percent of the inventive composition.

The antimicrobial component is that component of the composition that provides at least part of the antimicrobial activity, i.e., it has at least some antimicrobial activity for at least one microorganism. It is preferably present in a large enough quantity to be leached from the inventive composition and kill bacteria. If may also be biodegradable and/or made or derived from renewable resources such as plants or plant products. Biodegradable antimicrobial components can include at least one functional linkage such as an ester or amide linkage that con be hydrolytically or enzymatically degraded.

In certain embodiments, antimicrobial components arc non-ionic and have a hydrophile/lipophile balance (HLB) of at most 6.2, at most 5.8, or at most 5.5. Other preferred ranges for HLB are at least 3, least 3.2, or at least 3.4. The HLB may be determined from using the functional group contribution calculation shown in *Surfactant Systems,* Attwood, Chapman and Hall, London, 1983.

Certain antimicrobial components are uncharged and have an alkyl or alkenyl hydrocarbon chain containing at least 7 carbon atoms. For melt processing, preferred antimicrobial components have low volatility and do not decompose under process conditions. The preferred antimicrobial components contain less than 2 wt. % water, and more preferably less than 0.1.0 wt. % (determined by Karl Fischer analysis). Moisture content is kept low in Order to prevent hydrolysis of the aliphatic polyester and to,give clarity to extruded film. The moisture level should be similarly controlled for solvent cast films that are dried at elevated temperatures, e.g. greater than 50° C.-60° C.

The antimicrobial component content in the inventive composition (as it is ready to use) is typically at least 1 wt. %, 2 wt. %,5 wt. %, 10 wt. % and sometimes greater than 15 wt. %. In certain embodiments, in which a low strength is desired, the antimicrobial component comprises greater than 20 wt. %, greater than 25 wt. %, or even greater than 30 wt. % of the composition.

The antimicrobial component may include one or more fatty acid esters of a polyhydric alcohol, fatty ethers of a polyhydric alcohol, or alkoxylated derivatives thereof (of either or both of the ester and/or ether), or combinations thereof. More specifically, the antimicrobial component is selected from the group consisting of a (C7-C12)saturated fatty acid ester of a polyhydric alcohol (preferably, a (C8-C12)saturated fatty acid ester of a polyhydric alcohol), an (C8-C22) unsaturated fatty acid ester of a polyhydric alcohol (preferably, an (C12-C22) unsaturated fatty acid ester of a polyhydric alcohol), a (C7-C12) saturated fatty ether of a polyhydric alcohol (preferably, a (C8-C12) saturated fatty ether of a polyhydric alcohol), an (C8-C22) unsaturated fatty ether of a polyhydric alcohol (preferably, an (C12-C22) unsaturated fatty ether of a polyhydric alcohol), an alkoxylated derivative thereof, and combinations thereof. Preferably, the esters and ethers are monoesters and monoethers, unless they are esters and ethers of sucrose in which case they can be monoesters, diesters, monoethers, or diethers. Various combinations of monoesters, diesters, monoethers, and diethers can be used in a composition of the present invention.

Preferably the (C7-C12) saturated and (C8-C22) unsaturated monoesters and monoethers of polyhydric alcohols are at least 80% pure (having 20% or less diester and/or triester or diether and/or triether), more preferably 85% pure, even more preferably 90% pure, most preferably 95% pure. Impure esters or ethers would not have sufficient, if any, antimicrobial activity.

Useful fatty acid esters of a polyhydric alcohol may have the formula:

$$(R^1-C(O)-O)_n-R^2$$

wherein $R^1$ is the residue of a (C7-C12) saturated fatty acid (preferably, a (C8-C12) saturated fatty acid), or a (C8-C22) unsaturated (preferably, a C12-C22) unsaturated, including polyunsaturated) fatty acid, $R^2$ is the residue of a polyhydric alcohol (typically and preferably, glycerin, propylene glycol, and sucrose, although a wide variety of others can be used including pentaerythritol, sorbitol, mannitol, xylitol, etc.), and n= 1 or 2. The $R^2$ group includes at least one free hydroxy 1 group (preferably, residues of glycerin, propylene glycol, or sucrose). Preferred fatty acid esters of polyhydric alcohols are esters derived from C7, C8, C9, C10, C11, and C12 saturated fatty acids. For embodiments in which the polyhydric alcohol is glycerin or propylene glycol, n=1, although when it is sucrose, n=1 or 2. In general, monoglycerides derived from C10 to C12 fatty acids are food grade materials and GRAS materials.

Fatty acid esters are particularly useful candidates for treating food, and surfaces exposed to food, to reduce the number of human pathogens and spoilage in food since many of the monoesters have been reported to be food grade, generally recognized as safe (GRAS) materials, and have been reported to be effective as food preservatives and topical pharmaceutical agents. For example, Kabara, J. of Food Protection. 44:633-647 (1981) and Kabara, J. of Food Safety. 4:13-25 (1982) report that LAURICIDIN (the glycerol monoester of lauric acid commonly referred to as monolaurin), a food grade phenolic and a chelating agent may be useful in designing food preservative systems. Lauroyl ethylarginate is also approved by the FDA for use in foods.

Fatty acid monoesters, such as glycerol monoesters of lauric, caprylic, capric, and heptanoic acid and/or propylene glycol monoesters of lauric, caprylic, capric and heptanoic acid, are active against Gram positive bacteria, fungi, yeasts and lipid coated viruses but alone are not generally active against Gram negative bacteria. When the fatty acid monoesters are combined with the enhancers described below, the composition is active against Gram negative bacteria.

Certain of the antimicrobial components (e.g. fatty acid monoesters) can plasticize the aliphatic polyester. Exemplary fatty acid monoesters include, but are not limited to, glycerol monoesters of lauric (monolaurin), caprylic (monocaprylin), and capric (monocaprin) acid, and propylene glycol monoesters of lauric, caprylic, and capric acid, as well as lauric, caprylic, and capric acid monoesters of sucrose. Other fatty acid monoesters include glycerin and propylene glycol monoesters of oleic (18:1), linoleic (18:2), linolenic (18:3), and arachonic (20:4) unsaturated (including polyunsaturated) fatty acids. As is generally known, 18:1, for example, means the compound has 18 carbon atoms and 1 carbon-carbon double bond. Preferred unsaturated chains have at least one unsaturated group in the cis isomer form. In certain preferred embodiments, the fatty acid monoesters that are suitable for use in the present composition include known monoesters of lauric, caprylic, and capric acid, such as that known as GML or the trade designation LAURICIDIN (the glycerol monoester of lauric acid commonly referred to as monolaurin or glycerol monolaurate), glycerol monocaprate, glycerol monocaprylate, propylene glycol monolaurate, propylene glycol monocaprate, propylene glycol monocaprylate, and combinations thereof.

Exemplary fatty acid diesters of sucrose include, but are not limited to, lauric, caprylic, and capric diesters of sucrose as well as combinations thereof.

A fatty ether of a polyhydric alcohol is preferably of the formula:

$$(R^3-O)_n-R^4,$$

wherein $R^3$ is a (C7-C12)saturated aliphatic group (preferably, a (C8-C12) saturated aliphatic group), or a (C8-C22) unsaturated (preferably, (C12-C22) unsaturated, including polyunsaturated) aliphatic group, $R^4$ is the residue of a polyhydric alcohol. Preferred polyhydric alcohols include glycerin, sucrose, or propylene glycol. For glycerin and propylene glycol n=1, and for sucrose n=1 or 2. Preferred fatty ethers are monoethers of (C7-C12) alkyl groups (more preferably, (C8-C12) alkyl groups).

Exemplary fatty monoethers include, but are not limited to, laurylglyceryl ether, caprylglycerylether, caprylylglyceryl ether, laurylpropylene glycol ether, caprylpropyleneglycol ether, and caprylylpropyleneglycol ether. Other fatty monoethers include glycerin and propylene glycol monoethers of oleyl (18:1), linoleyl (18:2), linolenyl (18:3), and arachonyl (20:4) unsaturated and polyunsaturated fatty alcohols. In certain preferred embodiments, the fatty monoethers that are suitable for use in the present composition include laurylglyceryl ether, caprylglycerylether, caprylyl glyceryl ether, laurylpropylene glycol ether, caprylpropyleneglycol ether, caprylylpropyleneglycol ether, and combinations thereof. Unsaturated chains preferably have at least one unsaturated bond in the cis isomer form.

The alkoxylated derivatives of the aforementioned fatty acid esters and fatty ethers (e.g., one which is ethoxylated and/or propoxylated on the remaining alcohol groups) also have antimicrobial activity as long as the total alkoxylate is kept relatively low. Preferred alkoxylation levels are disclosed in U.S. Pat. No. 5,208,257. If the esters and ethers are ethoxylated, total moles of ethylene oxide are preferably less than 5, more preferably less than 2.

The fatty acid esters or fatty ethers of polyhydric alcohols can be alkoxylated, preferably ethoxylated and/or propoxylated, by conventional techniques. Alkoxylating compounds are preferably selected from the group consisting of ethylene oxide, propylene oxide, and mixtures thereof, and similar oxirane compounds.

The inventive compositions typically include, a total amount of fatty acid esters, fatty ethers, alkoxylated fatty acid esters, or alkoxylated fatty ethers of at least 1 weight percent (wt. %), at least 2 wt. %, greater than 5 wt. %, at least 6 wt.%, at least 7 wt. %, at least 10 wt.%, at least 15 wt. %, or at least 20 wt. %, based on the total weight of the ready-to-use composition. The term "ready-to-use" means the composition in its intended form for use, typically comprising less than 5 wt. % solvent or other volatile compounds that may have been used to make the inventive composition. In a preferred embodiment, they are present in a total amount of no greater than 60 wt. %, no greater than 50 wt. %, ho greater than 40 wt. %, or no greater than 35 wt.%, based on the total weight of the ready-to-use composition (i.e., excluding solvent). Alternatively, these proportions may be considered relative to the aliphatic polyester as 100 parts by weight, i.e., no greater than 150 parts fatty acid ester, 100 parts fatty acid ester, 67 parts fatty acid ester and 54 parts fatty acid ester. Certain compositions may be higher in concentration if they are intended to be used as a "masterbatch" for additional processing. As used herein, the term, "masterbatch" refers to a concentrate that is added to a composition that is melt processed or solvent cast.

Compositions of the present invention that include one or more fatty acid monoesters, fatty monoethers, hydroxyl acid esters of alcohols or alkoxylated derivatives thereof can also include a small amount of a di- or tri-fatty acid ester (i.e., a fatty acid di- or tri-ester), a di- or tri-fatty ether (i.e., a fatty di- or tri-ether), or alkoxylated derivative thereof. Preferably, such components comprise no more than 10 wt. %, no more than 7 wt. %, no more than 6 wt. %, or no more than 5 wt. %, of the total weight of the antimicrobial component. Thus, the monoester purity of the fatty acid monoester, fatty monoethers, hydroxyl acid esters of alcohols or alkoxylated derivatives thereof should exceed 85 %, preferably 90 %, and more preferably 95 %. For example, for monoesters, monoethers, or alkoxylated derivatives of glycerin, preferably there is no more than 10 wt. %, ho more than 7 wt. %, no more than 6 wt. %, or no more than 5 wt. % of a diester, diether, triester, triether, or alkoxylated derivatives thereof present, based on the total weight of the antimicrobial- (monoester or monoether) components present in the composition. Preferably, the triester or diester content is kept low to preserve the antimicrobial efficacy of the antimicrobial component.

An additional class of antimicrobial component is a fatty alcohol ester of a hydroxyl functional carboxylic acid preferably of the formula:

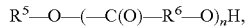

$R^5$—O—(—C(O)—$R^6$—O)$_n$H, wherein $R^5$ is the residue of a (C7-C14)saturated alkyl alcohol (preferably, a (C7-C12) saturated alkyl alcohol, more preferably, a (C8-C12) saturated alkyl alcohol) or a (C8-C22) unsaturated alcohol (including polyunsaturated alcohol), $R^6$ is the residue of a hydroxycarboxylic acid wherein the hydroxycarboxylic acid has the following formula:

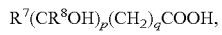

$R^7(CR^8OH)_p(CH_2)_qCOOH$, wherein: $R^7$ and $R^8$ are each independently H or a (C1-C8) saturated straight, branched, or cyclic alkyl group, a (C6-C12) aryl group, or a (C6-C12) aralkyl or alkaryl group wherein the alkyl groups, are saturated straight, branched, or cyclic, wherein $R^7$ and $R^8$ may be optionally substituted with one or more carboxylic acid groups; p=1 or 2; and q =0-3; and n=1, 2, or 3. The $R^6$ group may include one or more free hydroxyl groups but preferably is free of hydroxyl groups. Preferred fatty alcohol esters of hydroxycarboxylic acids are esters derived from branched or straight chain C8, C9, C10, C11, or C12 alkyl alcohols. The hydroxyacids typically have one hydroxyl group and one carboxylic acid group.

In one aspect, the antimicrobial component includes a (C7-C14) saturated fatty alcohol monoester of a (C2-C8) hydroxycarboxylic acid (preferably, a (C7-C12) saturated fatty alcohol monoester of a (C2-C8) hydroxycarboxylic acid, more preferably a (C8-C12) saturated fatty alcohol monoester of a (C2-C8) hydroxycarboxylic acid), a (C8-C22) mono- or poly-unsaturated fatty alcohol monoester of a (C2-C8) hydroxycarboxylic acid, an alkoxylated derivative of either of the foregoing, or combinations thereof. The hydroxycarboxylic acid moiety can include aliphatic and/or aromatic groups. For example, fatty alcohol esters of salicylic acid are possible. As used herein, a "fatty alcohol" is an alkyl or alkylene monofunctional alcohol having an even of odd number of carbon atoms.

Exemplary fatty alcohol monoesters of hydroxycarboxylic acids include, but are not limited to, (C6-C12) fatty alcohol esters of lactic acid such as octyl lactate, 2-ethylhexyl lactate (Purasolv EIIL from Purac, Lincolnshire Ill., lauryl lactate (Chrystaphyl 98 from Chemic Laboratories, Canton Mass.), lauryl lactyl lacate, 2-ethylhexyl lactyl lactate; (C8-C12) fatty alcohol esters of glycolic acid, lactic acid, 3-hydroxybutanoic acid, mandelic acid, gluconic acid, tartaric acid, and salicylic acid.

The alkoxylated derivatives of the fatty alcohol esters of hydroxy functional carboxylic acids (e.g., one which is ethoxylated and/or propoxylated on the remaining alcohol groups) also have antimicrobial activity as long as the total alkoxylate is kept relatively low. The preferred alkoxylation level is less than 5 moles, and more preferably less than 2 moles, per mole of hydroxycarboxylic acid.

The above antimicrobial components comprising an ester linkage are hydrolytically sensitive, and may be degraded by exposure to water, particularly at extreme pH (less than 4 or more than 10) or by certain bacteria that can enzymatically hydrolyze the ester to the corresponding acid and alcohol, which may be desirable in certain applications. For example, an article may be made to degrade rapidly by incorporating an antimicrobial component comprising at least one ester group. If extended persistence of the article is desired, an antimicrobial component, free of hydrolytically sensitive groups, may be used. For example, the fatty monoethers are not hydrolytically sensitive under ordinary processing conditions, and ate resistant to microbial attack.

Another class of antimicrobial components includes cationic amine antimicrobial compounds, which include antimicrobial protonated tertiary amines and small molecule quaternary ammonium compounds. Exemplary small molecule quaternary ammonium compounds include benzalkonium chloride and alkyl substituted derivatives thereof, di-long chain alkyl (C8-C18) quaternary ammonium compounds, cetylpyridinium halides and their derivatives, benzethonium chloride and its alkyl substituted derivatives, octenidine and compatible combinations thereof.

Cationic antiseptics and disinfectants useful as the antimicrobial component include small molecule quarternary ammonium compounds, typically comprising one or more quaternary ammonium group, having attached thereto at least one C6-C18 linear or branched alkyl or aralkyl chain. Suitable compounds include those disclosed in Lea & Febiger, Chapter 13 in Block, S., *Disinfection, Sterilization and Preservation*, 4$^{th}$ ed., 1991 and may have the formula:

$R^9R^{10}NR^{11}R^{12+}X^-$ in which $R^9$ and $R^{10}$ are C1-C18 linear or branched alkyl, alkaryl, or aralkyl chains that may be substituted by N, O or S provided at least one $R^9$or $R^{10}$ is a C8 -C18 linear of branched alkyl, alkaryl, or aralkyl moiety that may be substituted by N, O or S, R$H^{11}$ and $R^{12}$ are C1-C6 alkyl, phenyl, benzyl or C8-C12 alkaryl groups, or $R^{11}$ and $R^{12}$ may form a ring such as a pyridine ring with the N of the quaternary ammonium group, X is an anion, preferably halide such as Cl$^-$ or Br$^-$ but possibly methosulfate, ethosulfate, phosphate or similar anions. Compounds within this class are: monoalkyltrimethylammonium salts, monoalkyldimethyl-benzyl ammonium salts, dialkyldimethyl ammonium salts, behzethonium chloride, alkyl substituted benzethonium halides such as methylbenzethonium chloride and octenidine.

Examples of quaternary ammonium antimicrobial components are: benzalkonium halides having an alkyl chain length of C8-C18, preferably C12-C16, more preferably a mixture of chain lengths, e.g., benzalkoniumchloride comprising 40% C12 alkyl chains, 50% C14 alkyl chains, and 10% C16 chains (available as Barquat MB-50 from Lonza Group Ltd., Basel, Switzerland); benzalkonium halides substituted with alkyl groups oh the phenyl ring (available as Barquat 4250); dimethyldialkylammonium halides having C8-C18 alkyl groups, Or mixtures of such compounds (available as Bardac 2050, 205M and 2250 from Lonza); and cetylpyridinium halides such as cetylpyridinium chloride (Cepacol Chloride available as Cepacol Chloride from Merrell Labs); benzethonium halides and alkyl substituted benzethonium halides (available as Hyamine 1622 and Hyamine 10× from Rohm and Haas).

A useful class of cationic antimicrobials is based on protonated tertiary amines. Preferred cationic antimicrobial protonated tertiary amines have at least one C6-C18 alkyl group. Within this class are biodegradable derivatives of amino acids, as described in PCT publications WO 01/94292, WO 03/013454 and WO 03/034842, and combinations of those with sodium sorbate, potassium sorbate of sorbic acid, see WO 02/087328. These cationic antimicrobial components can be degraded in the environment or on living tissue. WO 03/013454 teaches such antimicrobial components having the formula

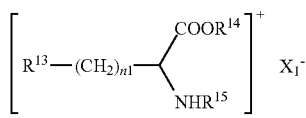

in which X may be Br$^-$, Cl$^-$ or HSO$_4^-$, R$^{15}$ may be a straight C8-C14 alkyl chain from an acid, e.g., saturated fatty hydroxy acid, R$^{14}$ is a C1-C18 straight chain or branched alkyl or an aromatic moiety; and R$^{13}$ may be —NH3,

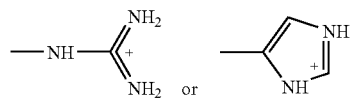

and n1 may be 0-4.

One useful member of this class of materials is lauroylethylarginate (the ethyl ester and lauric acid amide of the amino acid arginine (available as Mirenat N from A&B Ingredients, Fairfield, N.J.)). Methods for producing these compositions are disclosed in WO 01/94292.

The cationic antimicrobial components are typically added to the inventive compositions at a concentration of at least 1.0 wt. %, preferably at least 3 wt. %, more preferably greater than 5.0 wt. %, still more preferably at least 6.0 wt. %, even more preferably at least 10 wt. % and most preferably at least 20.0 wt. %, in some cases exceeding 25 wt. %. Preferably, the concentration is less than 50 wt. %, more preferably less than 40 wt. %, and most preferably less than 35 wt. %. Lower levels may be possible when used in combination with certain enhancers such as sorbic acid and/or its salts.

The antimicrobial components of this invention may be used alone or in combination in order to effectively kill microorganisms. Combinations of antimicrobial components that result in unstable compositions or that arc incompatible with each other should be avoided. For example, quaternary ammonium compounds may be incompatible with alkyl carboxylic acids or surfactants containing a sulfate moiety and/or sulfonic acid, and certain salts may cause precipitation of quaternary ammonium compounds.

As used herein, the term "antiseptic" refers to a substance that inhibits growth and reproduction of disease-causing microorganisms, especially those substances that may contact mammalian tissue such as skin, wounds, mucosal tissue and the like. In most cases, "antiseptic" is synonymous with antimicrobial when used to control mammalian pathogens. Antiseptics and antimicrobial components described herein may be used alone, in combination, or with other antimicrobial components. Additional antimicrobial components for use with those already described include peroxides, C6-C14 alkyl carboxylic acids and alkyl ester carboxylic acids, antimicrobial natural oils, polymeric biguanides (such as polyhexamethylene biguanide) and bisbiguanides (such as chlorhexidine and its salts including chlorhexidine gluconate) and compatible combinations thereof as mentioned in U.S. Patent Publication 20060051384. Other compatible antiseptics that may be used in combination with the inventive compositions on surfaces are iodine, iodophors, antimicrobial metals and metal salts such as silver salts and silver oxide, copper and zinc salts. In addition, certain antibiotics may be blended into the inventive compositions or coated on the surface of articles comprising them and include Neosporin, polymyxin, bacitracin, mupirocin, rifampin, minocycline, tetracycline, beta lactam antibiotics such as penicillin, methicillin and amoxicillin, fluoroquinolones, clindamycin, cephalosporins, macrolides, and aminoglycosides.

The inventive compositions may include an enhancer (preferably a synergist) to enhance the antimicrobial activity especially against Gram negative bacteria, e.g., E. coli and Psuedomonas sp. The chosen enhancer preferably affects the cell envelope of the bacteria. While not bound by theory, it is presently believed that the enhancer functions by allowing the antimicrobial component to more easily enter the cell cytoplasm and/or by facilitating disruption of the cell envelope. The enhancer component may include an alpha-hydroxy acid, a beta-hydroxy acid, other carboxylic acids, a (C2-C6) saturated or unsaturated alkyl carboxylic acid, a (C6-C16) aryl carboxylic acid, a (C6-C16) aralkyl carboxylic acid, a (C6-C12) alkaryl carboxylic acid, a phenolic compound (such as certain antioxidants and parabens), a (C5-C10) monohydroxy alcohol, a chelating agent, a glycol ether (i.e., ether glycol), or oligomers that degrade to release one of the above enhancers. Examples of such oligomers are oligomers of glycolic acid, lactic acid or both having at least 6 repeat units. Various combinations of enhancers can be used if desired.

The alpha-hydroxy acid, beta-hydroxy acid, and other carboxylic acid enhancers are preferably present in their protonated, free acid form. It is not necessary for all of the acidic enhancers to be present in the free acid form; however, the preferred concentrations listed below refer to the amount present in the free acid form. Additional, non-alpha hydroxy acid, betahydroxy acid or other carboxylic acid enhancers, may be added in order to acidify the formulation or buffer it at a pH to maintain antimicrobial activity. Preferably, acids are used having a pKa greater than about 2.5, preferably greater than about 3, and most preferably greater than about 3.5 in order to avoid hydrolyzing the aliphatic polyester component. Furthermore, chelator enhancers that include carboxylic acid-groups are preferably present with at least one, and more preferably at least two, carboxylic acid groups in their free acid form. The concentrations given below assume this to be the case. The enhancers in the protonated acid form are believed to not only increase the antimicrobial efficacy, but to improve compatibility when incorporated into the aliphatic polyester component.

One or more enhancers may be used in the compositions of the present invention at a suitable level to produce the desired result. Enhancers are typically present in a total amount greater than 0.1 wt. %, preferably in an amount greater than 0.25 wt; %, more preferably in an amount greater than 0.5 wt. %, even more preferably in an amount greater than 1.0 wt. %, and most preferably in an amount greater than 1.5 wt. % based on the total weight of the ready-to-use composition. In a preferred embodiment, they are present in a total amount of no greater than 10 wt-%, based on the total weight of the ready to use composition. Such concentrations typically apply to alpha-hydroxy acids, beta-hydroxy acids, other carboxylic acids, chelating agents, phenolics, ether glycols, and (C5-C10) monohydroxy alcohols.

The ratio of the enhancer component relative to the total concentration of the antimicrobial component is preferably within a range of. 10:1 to 1:300, and more preferably 5:1 and 1:10, on a weight basis.

The alpha-hydroxy acid is typically a compound of the formula:

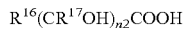

wherein: $R^{16}$ and $R^{17}$ are each independently H or a (C1-C8) alkyl group (straight, branched, or cyclic), a (C6-C12) aryl, or a (C6-C12) aralkyl or alkaryl group (wherein the alkyl group is straight, branched, or cyclic), $R^{16}$ and $R^{17}$ may be optionally substituted with one or more carboxylic acid groups; and n2=1-3, preferably, n2=1-2.

Exemplary alpha-hydroxy acids include, but are not limited to, lactic acid, malic acid, citric acid, 2-hydroxybutanoic acid, 3-hydroxybutanoic acid, mandelic acid, gluconic acid, glycolic acid, tartaric add, alpha-hydroxyethanoic acid, ascorbic acid, alpha-hydroxyoctanoic acid, and hydroxycaprylic: acid, as well as derivatives thereof (e.g., compounds substituted with hydroxyls, phenyl groups, hydroxyphenyl groups, alkyl groups, halogens, as well as combinations thereof). Preferred alpha-hydroxy acids include lactic acid, malic acid, and mandelic acid. These acids may be in D, L, or DL form and may be present as free acid, lactone, or partial salts thereof. All such forms are encompassed by the term "acid." Preferably, the acids are present in the free acid form. In certain preferred embodiments, the alpha-hydroxy acids useful in the compositions of the present invention, are selected from the group consisting of lactic acid, mandelic acid, malic acid, and mixtures thereof. Other suitable alpha-hydroxy acids are described in U.S. Pat. No. 5,665,776 (Yu).

One or more alpha-hydroxy acids may be incorporated in the inventive compositions, and/or applied to the surfaces of articles comprising the inventive composition, in an amount to produce the desired result They may be present in a total amount of at least 0.25 wt-%, at least 0.5 wt-%, and at least 1 wt-%, based on the total weight of the ready-to-use composition. They may be present in a total amount of no greater than 10 wt-%, no greater than 5 wt-%, or no greater than 3 wt-%, based oh the total weight of the ready-to-use composition.

The weight ratio of alpha-hydroxy acid enhancer to total antimicrobial component is at most 50:1, at most 30:1, at most 20:1, at most 10:1, at most 5:1 or at most 1:1. The ratio of alpha-hydroxy acid enhancer to total antimicrobial component may be at least 1:120, at least 1:80, or at least 1:60. Preferably the ratio of alpha-hydroxy acid enhancer to total antimicrobial component is within a range of 1:60 to 2:1.

A beta-hydroxy acid enhancer is typically a compound represented by the formula:

or

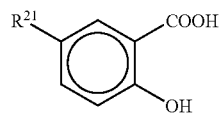

wherein: $R^{18}$, $R^{19}$, and $R^{20}$ are each independently H or a (C1-C8)alkyl group (saturated straight, branched, or cyclic group), (C6-C12) aryl, or (C6-C12) aralkyl or alkaryl group (wherein the alkyl group is straight, branched, or cyclic), $R^{18}$ and $R^{19}$ may be optionally substituted with one or more carboxylic acid groups; m=0 or 1; n3=1-3 (preferably, n3=1-2); and $R^{21}$ is H, (C1-C4) alkyl or a halogen.

Exemplary beta-hydroxy acids include, but are/not limited to, salicylic acid, beta-hydroxybutanoic acid, tropic acid, and trethocanic acid. In certain preferred embodiments, the beta-hydroxy acids useful in the compositions of the present invention are selected from the group consisting of salicylic acid, beta-hydroxybutanoic acid, and mixtures thereof. Other suitable beta-hydroxy acids are described in U.S. Pat. No. 5,665,776.

One or more beta-hydroxy acids may be used in the compositions of the present invention at a suitable level to produce the desired result. They may be present in a total amount of at least 0.1 wt-%, at least 0.25 wt-%, or at least 0.5 wt-%, based on the total weight of the ready-to-use composition. They may also be present in a total amount of no greater than 10 wt-%, no greater than 5 wt-%, and no greater than 3 wt-%, based on the total weight of the ready-to-use composition. Higher concentrations may become irritating to tissue. Alternatively, beta-hydroxy acids may be applied to the surface, of articles comprising the inventive composition. When present on the surface, the levels may be 0.05 wt. %, preferably 0.1 wt. %, more preferably 0.25 wt. %, and most, preferably 0.5 wt. % of the article.

The weight ratio of beta-hydroxy acid enhancer to total antimicrobial component is preferably at most 50:1, at most 30:1, at most 20:1, at most 10:1, at most 5:1, or The ratio of beta-hydroxy acid enhancer to total antimicrobial component is preferably at least 1:120, at least 1:80, or at least 1:60. Preferably the ratio of beta-hydroxy acid enhancer to total antimicrobial component is within a range of 1:60 to 2:1, more preferably 1:15 to 1:1.

In systems with low concentrations of water, or that are essentially free of water, transesterification may be the principle route of loss of the fatty acid monoester and alkoxylated derivatives of these active ingredients and loss of carboxylic acid containing enhancers may occur due to esterification. Thus, certain alpha-hydroxy acids (AHA) and beta-hydroxy acids (BHA) are particularly preferred since these are believed to be less likely to transesterify the ester antimicrobial or other ester by reaction of the hydroxyl group of the AHA or BHA. For example, salicylic acid may be particularly preferred in certain formulations since the phenolic hydroxyl group is a much more acidic alcohol and thus much less likely to react. Other particularly preferred compounds in anhydrous or low-water content formulations include lactic, mandelic, malic, citric, tartaric, and glycolic acid. Benzoic acid and substituted benzoic acids that do not include a hydroxyl group, while not hydroxyl acids, are also preferred due to a reduced tendency to form ester groups. This applies to both melt and solvent cast processable systems or compositions.

Carboxylic acids other than alpha- and beta-carboxylic acids are suitable enhancers. They include alkyl, aryl, aralkyl, or alkaryl carboxylic acids typically having equal to or less than 12 carbon atoms. A preferred class of these can be represented by the following formula:

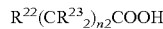

$R^{22}(CR^{23}_2)_{n2}COOH$ wherein: $R^{22}$ and $R^{23}$ are each independently H or a (C1-C4) alkyl group (which can be a straight, branched, or cyclic group), a (C6-C12) aryl group, a (C6-C12) group containing both aryl groups and alkyl groups (which can be a straight, branched, or cyclic group), $R^{22}$ and $R^{23}$ may be optionally substituted with one or more carboxylic acid groups and n2=0-3, preferably, n2=0-2. The carboxylic acid may be a (C2-C6) alkyl carboxylic acid, a (C6-C16) aralkyl carboxylic acid, or a (C6-C16) alkaryl carboxylic acid. Exemplary acids include, but are not limited to acetic acid, propionic acid, sorbic acid, benzoic acid, benzylic acid, and nonylbenzoic acid.

One or more such carboxylic acids may be used in the compositions of the present invention in amounts sufficient to produce the desired result. In certain embodiments, they are present in a total amount no greater than 5 wt-%, preferably no greater than 3 wt-%, based on the total weight of the ready-to-use composition.

Alternatively, carboxylic acid enhancers may be present on the surface of an article made from the inventive composition. When present on the surface, the amounts used may be 0.05 wt. %, prefebably 0.1 wt. %, more preferably 0.25 wt. %, and most preferably 0.5 wt. % of the article.

The weight ratio of the total concentration of carboxylic acids (other than alpha- or beta-hydroxy acids) to the total concentration of the antimicrobial component is preferably within a range of 10:1 to 1:100, and preferably 2:1 to 1:10.

A chelating agent (i.e., chelator) is typically an organic compound capable of multiple coordination sites with a metal ion in solution. Typically these chelating agents are polyanionic compounds and coordinate best with polyvalent metal ions. Exemplary chelating agents include, but are not limited to, ethylene diamine tetraacetic acid (EDTA) and salts thereof (e.g., EDTA(Na)$_2$, EDTA(Na)$_4$, EDTA(Ca), EDTA(K)$_2$), sodium acid pyrophosphate, acidic sodium hexametaphosphate, adipic acid, succinic acid, polyphosphoric acid, sodium acid pyrophosphate, sodium hexametaphosphate, acidified sodium hexametaphosphate, nitrilotris (methylenephosphonic acid), diethylenetriaminepentaacetic acid, 1-hydroxyethylene, 1,1-diphosphonic acid, and diethylenetriaminepenta-(methylenephosphonic acid). Certain carboxylic acids, particularly the alpha-hydroxy acids and beta-hydroxy acids, can also function as chelators, e.g., malic acid and tartaric acid.

Also included as chelators are compounds highly specific for binding ferrous and/or ferric ion such as siderophores, and iron binding proteins. Iron binding protein include, for example, lactoferrin, and transferrin. Siderophpres include, for example, enterochlin, enterobactin, vibriobactin, anguibactin, pyochelin, pyoverdin, and aerobaetin.

In certain embodiments, the chelating agents useful in the compositions of the present invention include those selected from the group consisting of ethylenediaminetetraacetic acid and salts thereof, succinic acid, and mixtures thereof. Preferably, either the free acid or the mono- or di-salt form of EDTA is used.

One or more chelating agents may be used in the compositions of the present invention at a suitable level to produce the desired result. They may be used in amounts similar to the carboxylic acids described above.

The ratio of the total concentration of chelating agents (other than alpha- or beta-hydroxy acids) to the total concentration of the antimicrobial component is preferably within a range of 1.0:1 to 1:100, and more preferably 1:1 to 1:10, on a weight basis.

A phenolic compound enhancer is typically a compound having the following general structure:

wherein: m2 is 0 to 3 (especially 1 to 3), n4 is 1 to 3 (especially 1 to 2), each $R^{24}$ independently is alkyl or alkenyl of up to 12 carbon atoms (especially up to 8 carbon atoms) optionally substituted with O in of on the chain (e.g., as a carbonyl group) or OH on the chain, and each $R^{25}$ independently is H or alkyl or alkenyl of up to 8 carbon atoms (especially up to 6 carbon atoms) optionally substituted with O in or on the chain (e.g., as a carbonyl group) or OH on the chain, but if $R^{25}$ is H, n4 preferably is 1 or 2.

Examples of phenolic enhancers include, but are not limited to, butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, 4,6-di-tert-butyl-resorcinol, methyl paraben (4-hydroxybenzoic acid methyl ester), ethyl paraben, propyl paraben, butyl paraben, 2-phenoxyethanol, as well as combinations thereof. One group of the phenolic compounds is the phenol species having the general structure shown above where $R^{25}$ is H and where $R^{24}$ is alkyl or alkenyl of up to 8 carbon atoms, and n4 is 0, 1, 2, or 3, especially where at least one $R^{24}$ is butyl and particularly tert-butyl, and especially the non-toxic members thereof being preferred. Some of the phenolic synergists are BHA, BHT, methyl paraben, ethyl paraben, propyl paraben, and butyl paraben as well as combinations of these.

One or more phenolic compounds may be used in the compositions of the present invention at a suitable level to produce the desired result. The concentrations of the phenolic compounds may vary widely, but typically greater than 0.5 wt. %, based oh the total weight of the composition, can be effective when the above-described esters are present within the above-noted ranges. In some embodiments, they are present in a total amount of at least 0.75 wt-%, or at least 1.0 wt-%,based on the total weight of the composition. In other embodiments, they are present in a total amount of no greater than 8 wt-%, no greater than 4 wt%, or no greater than 2 wt-%, based on the ready to use composition.

In commercially available PLA (poly(lactic acid)), antioxidant may be present, e.g., about 0.25-0.50 wt. %. When antioxidants are added to an aliphatic polyester, the antioxidants are believed tobe uniformly mixed (and perhaps dissolved) within the material, with a minimal amount on the surface to enhance antimicrobial activity. Significantly lower concentrations of phenolics are typically employed for antioxidant use (e.g., not more than 0.1%) than are employed when using as an enhancer for me antimicrobial component (e.g., greater than 1%). The phenolic compounds may be present on the surface of the composition. When present on the surface, the levels may be at least 0.05 wt. %, preferably at least 0.1 wt. %, more preferably at least 0.25 wt. %, and most preferably at least 0.5 wt. % of the article to which they are applied.

The weight ratio of the total phenolic concentration to the total concentration of the antimicrobial component may be within a range of 1:1 to 1:100, or preferably within a range of 1:1 to 1:10, on a weight basis.

The above-noted concentrations of the phenolics are normally observed unless concentrated formulations for subsequent dilution are intended. The minimum concentration of the phenolics and the antimicrobial components to provide an antimicrobial effect will vary with the particular application.

An additional enhancer is a monohydroxy alcohol having 5-10 carbon atoms, including C5-C10 monohydroxy alcohols (e.g., octanol and decanol). In certain embodiments, alcohols useful in the compositions of the present invention are selected from the group n-pentanol, 2 pentanol, n-hexanol, 2 methylpentyl alcohol, n-octanol, 2-ethylhexyl alcohol, decanol, and mixtures thereof.

C5-C10 alcohols may be present in a total amount of at least 1 wt. %, at least 2 wt; %, at least 3 wt. %, or at least 5 wt. %, based on the composition. C5-C10 alcohols may be present in a total amount of no greater than 20 wt-%, no greater than 15 wt-%, or no greater than 10 wt-%, based on the total weight of the composition. C5-C10 alcohols may be applied to the surface of articles comprising the composition of polymer and antimicrobial component. When present on the surface, amounts may be at least 0.05 wt: %, preferably at least 0.1 wt. %, more preferably at least 0.25 wt. %, and most preferably at least 0.5 wt. % of the article to which the composition is applied.

An additional enhancer is an ether glycol. Exemplary ether glycols include those of the formula:

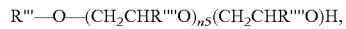

R'''—O—(CH$_2$CHR''''O)$_{n5}$(CH$_2$CHR''''O)H, wherein R'''=H, a (C1-C8) alkyl, or a (C6-C12) aralkyl or alkaryl; and each R'''' is independently=H, methyl, or ethyl; and n5=0-5, preferably 1-3. Examples include 2-phenoxyethanol, dipropylene glycol, triethylene glycol, the line of products available under the trade designation DOWANOL DB (di(ethylene glycol) butyl ether), DOWANOL DPM (di(propylene glycol)monomethyl ether), and DOWANOL TPnB (tri(propylene glycol) monobutyl ether), as well as many others available from Dow Chemical Company, Midland Mich.

One or more ether glycols may be present in a total amount of at least 0.5 wt. %, based on the total ready-to-use composition. In an embodiment, they are present in a total amount of no greater than 20 wt-%, based on the total weight of the ready-to-use composition. The ether glycols may be present on the surface of articles comprising the inventive composition. When present on the surface, the amounts may be at least 0.05 wt. %, preferably at least 0.1 wt. %, more preferably at least 0.25 wt. %, and, most preferably at least 0.5 wt. % of the articles to which the glycols are applied as part of the inventive composition.

Oligomers that release an enhancer may be prepared by a number of methods. For example, oligomers may be prepared from alpha hydroxy acids, beta hydroxy acids, or mixtures thereof by standard esterification techniques. Typically, these oligomers have at least two hydroxy acid units, preferably at least 10 hydroxy acid units, and most preferably at least 50 hydroxy acid units. For example, a copolymer of lactic acid and glycolic acid may be prepared as shown in the Examples section.

Alternatively, oligomers of (C2-C6) dicarboxylic acids and diols may be prepared by standard esterification techniques, these oligomers preferably have at least 2 dicarboxylic acid units; preferably at least 10 dicarboxylic acid units, and most preferably at least 50 dicarboxylic acid units.

The enhancer releasing oligomeric polyesters used typically have a weight average molecular weight of less than 10,000 daltons and preferably less than 8,000 daltons.

These oligomeric polyesters may be hydrolyzed. Hydrolysis can be accelerated by an acidic or basic environment, for example at a pH less than 5 or greater than 8. The oligomers may be degraded, enzymatically by enzymes present in the composition or in the environment in which it is used, for example from mammalian tissue or from microorganisms in the environment.

Compositions of the present invention can include one or more surfactants to promote compatibility of the composition and to help wet the surface and/or to aid in contacting and killing microorganisms. As used, herein the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like. The surfactant can be cationic, anionic, nonionic, or amphoteric. In applications in which biodegradability is important, it may be desirable to incorporate biodegradable surfactants, which typically include ester and/or amide groups that may be hydrolytically or enzymatically cleaved. A variety of conventional surfactants may be used; however, certain ethoxylated surfactants can reduce or eliminate the antimicrobial efficacy of some of the antimicrobial lipid components.

The reason for this effect is hot known and not all ethoxylated surfactants display this negative effect. For example, poloxamer (polyethylene oxide/polypropylene oxide) surfactants have been shown to be compatible with the antimicrobial lipid component, but ethoxylated sorbitan fatty acid esters such as those sold under the trade name TWEEN by ICI have not been compatible. It should be noted that these are broad generalizations and the activity could be formulation dependent. One skilled in the art can determine compatibility of a surfactant by making the formulation and testing for antimicrobial activity as described in the Examples herein. Combinations of various surfactants can be used.

Certain antimicrobial components are amphiphiles and may be surface active, For example, certain antimicrobial alkyl monoglycerides described herein are surface active. For certain embodiments of the invention, the antimicrobial lipid component is considered distinct from a surfactant component.

Surfactants that have an HLB (i.e., hydrophile to lipophile balance) of at least 4 or at least 8 are preferred. More preferred surfactants have an HLB of at least 12. Most preferred surfactants have an HLB of at least 15.

Examples of the various classes of surfactants are described below. In certain preferred embodiments, the surfactants useful in the compositions of the present invention are selected from the group consisting of sulfonates, sulfates, phosphonates, phosphates, poloxamers (polyethylene oxide/polypropylene oxide block copolymers), alkyl lactates, alkyl carboxylates, aralkyl carboxylates, alkylethoxylated carboxylates, aralkylethoxylated carboxylates, cationic surfactants, and mixtures thereof. In certain more preferred embodiments, the surfactants useful in the compositions of the present invention are selected from the group consisting of sulfonates, sulfates, phosphates, and mixtures thereof. In one aspect, the surfactant is selected from (C8-C22) alkyl sulfate salts (e.g., sodium salt), di(C8-C13 alkyl)sulfosuccinate salts, C8-C22 alkyl sarconsinate, and combinations thereof.

One or more surfactants may be used in and/or on the compositions of the present invention at a suitable level to produce the desired result. In some embodiments, when used in the composition, they are present in a total amount of at least 0.1 wt-%, at least 0.5 wt-%, or at least 1.0 wt-%, based on the total weight of the ready-to-use composition. In other embodiments, they are present in a total amount of no greater than 20 wt-%, no greater than 15 wt-%, no greater than 10 wt-%, or no greater than 5 wt-%, based on the total weight of the ready to use composition. The ratio of the total concentration of surfactant to the total concentration of the antimicrobial component may be within a range of 5:1 to 1:100, from 3:1 to 1:10, or from 2:1 to 1:3, on a weight basis. The surfactants may be present on the surface of an article comprising the inventive composition. When present on the surface, amounts may be 0.05 wt. %, preferably 0.1 wt. %, more preferably 0.25 wt. %, and most preferably 0.5 wt., % of the article to which the surfactant is applied.

Exemplary cationic surfactants include, but are not limited to, salts of optionally polyoxyalkylenated primary, secondary, or tertiary fatty amines; quaternary ammonium salts such as tetraalkylammonium, alkylamidoalkyltrialkylammonium, trialkylbenzylammonium, trialkylhydroxyalkylammonium, or alkylpyridinium halides (chlorides or bromides) as well as other anionic counterions, such as but not limited to, alkyl sulfates, such as but not limited to, methosulfate and ethosulfate; imidazoline, derivatives; amine oxides of a cationic nature (e.g., at an acidic pH).

The cationic surfactants may be selected from the group consisting of tetralkyl ammonium, trialkylbenzylammonium, and alkylpyridinium halides as well as other anionic counterions, such as but not limited to, C1-C4 alkyl sulfates, such as but not limited to, methosulfate and ethosulfate, and mixtures thereof.

Amine oxide surfactants may be used including alkyl and alkylamidoalkyldialkylamine oxides of the following formula:

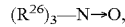

wherein $R^{26}$ is a (C1-C30) alkyl group (preferably a (C1-C14) alkyl group) or a (C6-C18) aralklyl or alkaryl group, wherein any of these groups can be optionally substituted in or on the chain by N-, O-, or S-containing groups such as amide, ester, hydroxyl, and the like. Each $R^{26}$ may be the same or different provided at least one $R^{26}$ group includes at least eight carbons. Optionally, the $R^{26}$ groups can be joined to form a heterocyclic ring with the nitrogen to form surfactants such as amine oxides of alkyl morpholine, alkyl piperazine, and the like. In one such surfactant, two $R^{26}$ groups are methyl and one $R^{26}$ group is a (C12-C16)alkyl of alkylamidopropyl group. Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Company (Northfield, Ill.).

Exemplary anionic surfactants include, but are not limited to, sarcosinates, glutamates, alkyl sulfates, sodium or potassium alkyleth sulfates, ammonium alkyleth sulfates, ammonium laureth-n-sulfates, laureth-n-sulfates, isethionates, glycerylether sulfonates, sulfosuccinates, alkylglyceryl ether sulfonates, alkyl phosphates, aralkyl phosphates, alkylphosphonates, and aralkylphosphonates. These anionic surfactants may have a metal or organic ammonium counterion. Certain useful anionic surfactants are selected from the group consisting of: sulfonates and sulfates such as alkyl sulfates, alkylether sulfates, alkyl sulfonates, alkylether sulfonates, alkylbenzene sufonates, alkylbenzene ether sulfates, alkylsulfoacetates, secondary alkane sulfonates, secondary alkylsulfates, and the like. Many of these can be represented by the formulas:

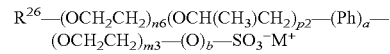

and

wherein: a and b=0 or 1; n6, p2, and m3=0-100 (preferably 0-20); $R^{26}$ is defined as above provided at least one $R^{26}$ or $R^{27}$ is at least C8; $R^{27}$ is a (C1-C12)alkyl group (saturated straight, branched, or cyclic group) that may be optionally substituted by N, O, or S atoms or hydroxyl, carboxyl, amide, or amine groups; Ph=phenyl; and M is a cationic counterion such as H, Na, K, Li, ammonium, or a protonated tertiary amine such as triethanolamine or a quaternary ammonium group.

In the formula above, the ethylene oxide groups (i.e., the "n6" and "m3" groups) and propylene oxide groups (i.e., the "p2" groups) can occur in reverse order as well as in a random, sequential, or block arrangement. $R^{26}$ may be an alkylamide group such as $R^{28}$—C(O)N(CH$_3$)CH$_2$CH$_2$— as well as ester groups such as —OC(O)—CH$_2$— wherein $R^{28}$ is a (C8-C22)alkyl group (branched, straight, or cyclic group). Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14-C17)secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16)fatty acid available from Stepan Company under the trade designation ALPHASTEP PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammonium-lauryl sulfate commercially available under the trade designation STEPANOL AM from Stepan Company; dialkylsulfosuccinates such as dioctylsodiumsulfosuccinate available as Aerosol OT from Cytec Industries.

Suitable anionic surfactants also include phosphates such as alkyl phosphates, alkylether phosphates, aralkylphosphates, and aralkylether phosphates. Many may be represented by the formula:

$$[R^{26}-(Ph)_a-O(CH_2CH_2O)_{n6}(CH_2CH(CH_3)O)_{p2}]_{q2}-P(O)[O^-M^+]_r,$$

wherein: Ph, $R^{26}$, a, n6, p2, and M are defined above; r is 0-2; and q2=1-3; with the proviso that when q2=1, r=2, and when q2=2, r=1, and when q2=3, r=0. As above, the ethylene oxide groups (i.e., the "n6" groups) and propylene oxide groups (i.e., the "p2" groups) can occur in reverse order as well as in a random, sequential, or block arrangement. Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J., and mixtures thereof.

Surfactants of the amphoteric type include surfactants having tertiary amine groups, which may be protonated, as well as quaternary amine containing zwitterionic surfactants. Examples include:

Ammonium Carboxylate Amphoterics. This class of surfactants can be represented by the following formula:

$$R^{29}-(C(O)-NH)_a-R^{30}-N^+(R^{31})_2-R^{32}-COO^-,$$

wherein: a=0 or 1; $R^{29}$ is a (C1-C21) alkyl group (saturated or unsaturated straight, branched, or cyclic group), (C6-C22) aryl group, or (C6-C22) aralkyl or alkaryl group (saturated straight, branched, or cyclic alkyl group), wherein $R^{29}$ may be optionally substituted with one or more N, O, or S atoms, or one or more hydroxyl, carboxyl, amide, or amine groups; $R^{31}$ is H or a (C1-C8)alkyl group (saturated or unsaturated straight, branched, or cyclic group), wherein $R^{31}$ may be optionally substituted with one or more N, O, or S atoms, or one or more hydroxyl, carboxyl, amine groups, a (C6-C9) aryl group, or a (C6-C9)aralkyl or alkaryl group; and $R^{30}$ and $R^{32}$ are each independently a (C1-C10) alkylene group that may be the same or different and may be optionally substituted with one or more N, O, or S atoms, or one or more hydroxyl or amine groups.

In the formula above, $R^{29}$ may be a (C1-C18) alkyl group, $R^{31}$ may be a (C1-C2) alkyl group possibly substituted with a methyl, benzyl group or a methyl group. When $R^{31}$ is H, the surfactant, at higher pH values, could exist as a tertiary amine with a cationic counterion such as Na, K, Li, or a quaternary amine group.

Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1L, MACKAM 2L, and MACKAM 151L, respectively, from McIntyre Group Ltd.).

Ammonium Sulfonate Amphoterics. This class of amphoteric surfactants are referred to as "sultaines" or "sulfobetaines" and can be represented by the following formula:

$$R^{29}-(C(O)-NH)_a-R^{30}-N^+(R^{31})_2-R^{32}-SO_3^-,$$

wherein $R^{29}-R^{32}$ and "a" are defined above. Examples include cocamidopropylhydroxysultaine (commercially available as MACKAM 50-SB from McIntyre Group Ltd.). The sulfoamphoterics may be preferred over the carboxylate amphoterics since the sulfonate group will remain ionized at much lower pH values.

N-acyl amide carboxylate surfactants can be represented by the following formula:

$$R^{33}-C(O)-NR^{34}CH_2-COOM,$$

wherein: $R^{33}$ is a (C7-C21) alkyl group (saturated or unsaturated straight, branched, or cyclic group), a (C6-C22) aryl group, or a (C6-C22) aralkyl or alkaryl group (saturated straight, branched, or cyclic alkyl group), wherein $R^{33}$ may be optionally substituted with one or more N, O, or S atoms, or one or more hydroxyl, carboxyl, amide, or amine groups; $R^{34}$ is H or a (C1-C3) alkyl group (saturated straight or branched group). M is defined above: Examples include lauroyl sarcosine, myristoyl sarcosine, oleyl sarcosine, lauroyl glycine, N-Methyl-N-(1-oxododecyl) glycine, and the like. N-acyl sarcosinates are available from Croda Inc. Edison, N.J. This class of surfactants is particularly appealing for biodegradable applications since they are readily degraded especially at alkaline pH.

Nonionic surfactants include, but are not limited to, alkyl glucosides, alkyl polyglucosides, polyhydroxy fatty acid amides, sucrose esters, esters of fatty acids and polyhydric alcohols, fatty acid alkanolamides, ethoxylated fatty acids, ethoxylated aliphatic acids, ethoxylated fatty alcohols (e.g., octyl phenoxy polyethoxyethanol available under the trade, name TRITON X-100 and nonyl phenoxy poly(ethyleneoxy) ethanol available under the trade name NONIDET P-40, both from Sigma Chemical Company, St. Louis, Mo.), ethoxylated and/or propoxylated aliphatic alcohols (BRIJ from ICI, Wilmington, Del.), ethoxylated glycerides, ethoxylated/propoxylated block copolymers such as PLURONIC and TETRONIC surfactants (BASF), ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants (FLUORAD-FS 300 surfactant from 3M Company, St. Paul, Minn., and ZONYL from Dupont de Nemours Company, Wilmington, Del.) and polymerizable (reactive) surfactants (e.g., SAM 211 (alkylene polyalkoxy sulfate) surfactant available under the trade name MAZON surfactants useful in the compositions of the present invention are selected from the group consisting of Poloxamers such as PLURONIC from BASF, sorbitan fatty acid esters, and mixtures thereof.

Additionally, the compositions may further comprise organic and, inorganic fillers. For implantable applications biodegradable, resorbable, or bioerodible inorganic fillers may be particularly appealing. These materials may help to control the degradation rate of the polymer composition. For example, many calcium salts and phosphate salts may be suitable. Exemplary biocompatible resorbable fillers include calcium carbonate, calcium sulfate, calcium phosphate, calcium sodium phosphates, calcium potassium phosphates, tetracalcium phosphate, .alpha.-tricalcium phosphate, beta-tricalcium phosphate, calcium phosphate apatite, oetacalcium phosphate, dicalcium phosphate, calcium carbonate, calcium oxide, calcium hydroxide, calcium sulfate dihydrate, calcium sulfate hemihydrate, calcium fluoride, calcium citrate, magnesium oxide, and magnesium hydroxide. A particularly suitable filler is tribasic calcium phosphate (hydroxy apatite).

Articles comprising the inventive composition may be made by processes known in the art for making products like polymer sheet from polymer resins. For many applications, such articles can be placed in water at 23° C. without substantial loss of physical integrity (e.g. tensile strength) after being immersed 2 hours and dried. Typically, these articles contain little or no water. The water content in the article after extruding, injection molding or solvent casting is typically less than 10% by weight, preferably less than 5% by weight, more preferably less than 1% by weight and most preferably less than 0.2% by weight. Polymeric sheets may be formed by an extrusion process from the inventive resin compositions, resulting in antimicrobial polymer sheets useful in applications such as food wrapping. Other articles that may be made of the inventive composition may include medical drapes and gowns, including surgical drapes, procedural drapes, plastic specialty drapes, incise drapes, barrier drapes, barrier gowns, SMS gowns, and the like, wound dressings, wound absorbents, wound contact layers, surgical sponges use to absorb blood and body fluids during surgery, surgical implants, vascular catheters, urinary catheters, endotracheal tubes, shunts, wound drains and other medical devices. Articles made of the inventive compositions may be solvent, heat, or ultrasonically welded together as well as being welded to other compatible articles. The inventive compositions may be used in conjunction with other materials to form constructions such as sheath/core materials, laminates, compound structures of two or more materials, or useful as coatings on various medical devices. The compositions of the present invention may be useful in the fabrication of surgical sponges.

The inventive compositions are particularly suitable for use in surgical drapes and gowns due to their unique combination of properties. For example, the polylactic acid/antimicrobial component compositions have exceptional antimicrobial activity as described herein. Non-woven web and sheets comprising the inventive compositions have good tensile strength; can be heat sealed to form strong bonds allowing specialty drape fabrication; can be made from renewable resources which can be important in disposable products; can have high surface energy to allow wettability and fluid absorbency in the case of non-wovens (contact angles with distilled water often are less than 50 degrees, preferably less than 30 degrees, and most preferably less than 20 degrees when measured on a flat film using the half angle technique described in U.S. Pat. No. 5,268,733 and a Tantec Contact Angle Meter, Model CAM-micro, Schamberg, Ill. In order to determine the contact angle of materials other than films a film of the exact same composition should be made by solvent casting the composition as described in the examples). It is believed that such webs can be sterilized by gamma radiation of electron beam without significant loss of physical strength (tensile strength for a 1 mil thick film does not decrease by more than 20% and preferably by not more than 10% after exposure to 2.5 Mrad gamma radiation from a cobalt gamma radiation source and aged at 23°-25° C. for 7 days. Additional melt additive (e.g., fluorochemical melt additive) can be added to the composition to decrease surface energy (increase the contact angle) and impart repellency. When repellency is desired the contact angle measured on a flat film using the half angle technique as described above is preferably greater than 70 degrees, preferably greater than 80 degrees and most preferably greater than 90 degrees.

The release of an antimicrobial component of the inventive composition may improve articles such as wound and surgical dressings by helping to prevent bacterial growth or attachment. The rate of release of antimicrobial components from the aliphatic polyester may be affected by incorporation of plasticizers, surfactants, emulsifiers, enhancers, humectants, as well as other components. Suitable humectants may include/polyhydric alcohols such as glycerol, propylene glycol, dipropylene glycol, polypropylene glycol, polyethylene glycol, diethylene glycol, pentaerythritol, trimethylolpropane, trimethylolethane, trimethylolbutane, sorbitol, mannitol, xylitol, pantothenol, ethylene glycol adducts of polyhydric alcohol, propylene oxide adducts of polyhydric alcohol, 1,3-butanediol, dipropylene glycol, diglycerine, polyglycerine, erythritol, sorbitan, sugars (e.g., sucrose, glucose, fructose, mannose, xylose, saccharose, trehalose), sugar alcohols, and the like. Potentially useful polyhydric alcohols include glycols (i.e., those containing two hydroxyl groups) including glycerin and propylene glycol.

Other medical devices that may be made in whole or in part, of the inventive composition include: sutures, suture fasteners, surgical mesh, slings; orthopedic pins (including bone filling augmentation material), adhesion barriers, stents, guided tissue repair/regeneration devices, articular cartilage repair devices, nerve guides, tendon repair devices, atrial septal defect repair devices, pericardial patches, bulking and filling agents, vein valves, bone marrow scaffolds, meniscus regeneration devices, ligament and tendon grafts, ocular cell implants, spinal fusion cages, skin substitutes, dural substitutes, bone graft substitutes, bone dowels, and hemostats.

If the inventive composition is used in a wound dressing backing film, the film may be partially (e.g. zone or pattern) coated or completely coated with various adhesives, including but not limited to pressure sensitive adhesives (PSAs), such as acrylic and block copolymer adhesives, hydrogel adhesives, hydrocolloid adhesives, and foamed adhesives. PSAs can have a relatively high moisture vapor transmission rate to allow for moisture evaporation. Suitable pressure sensitive adhesives include those based on acrylates, polyurethanes, KRATON and other block copolymers, silicones, rubber based adhesives as well as combinations of these adhesives. The preferred PSAs are the normal adhesives that are applied to skin such as the acrylate copolymers described in U.S. Pat. No. RE 24,906, the disclosure of which is hereby incorporated by reference, particularly a 97:3 iso-octyl acrylate:acrylamide copolymer. Also preferred is an 70:15:15 isooctyl aerylate-ethylenepxide:acrylate:acrylic acid terpolymer, as described in U.S. Pat No. 4,737,410 (Example 31), the disclosure of which is hereby incorporated by reference. Other useful adhesives are described in U.S. Pat. Nos. 3,389,827, 4,112,213, 4,310,509 and 4,323,557, the disclosures of which are hereby incorporated by reference. Inclusion of medicaments or antimicrobial agents in the adhesive is also contemplated, as described in U.S. Pat. Nos. 4,310,509 and 4,323,557.

In one process for making the inventive antimicrobial composition, the aliphatic polyester in a melt form is mixed in a sufficient amount relative to the antimicrobial component to yield a polymer composition having measurable antimicrobial activity. An enhancer and/or surfactant may be added; to the melt polymer composition and/or coated on the surface of an article comprising the polymer composition to enhance the antimicrobial component.

A variety of equipment and techniques are known in the art for melt processing polymeric compositions. Such equipment and techniques are disclosed, for example, in U.S. Pat. No. 3,565,985 (Schrenk et al.), U.S. Pat. No. 5,427,842 (Bland et. al.), U.S. Pat. Nos. 5,589,122 and 5,599,602 (Leonard), and U.S. Pat. No. 5,660,922 (Henidge et al.). Examples of melt processing equipment include, but are hot limited to, extruders (single and twin screw), Banbury mixers, and Brabender extruders for melt processing the inventive composition.

The ingredients of the composition may be mixed in and conveyed through an extruder to yield a polymer composition having measurable antimicrobial activity, preferably without polymer degradation or side reactions in the melt. The processing temperature is sufficient to mix the biodegradable aliphatic polyester and antimicrobial component, and allow extruding the composition as a film. Potential degradation reactions include transesterification, hydrolysis, chain scission and radical chain decomposition, and process conditions should minimize such reactions. The inventive film has properties that are desirable in applications such as food wrap, e.g., transparent (not hazy) and being free of oily residue on the surface (which might indicate phase separation of the antimicrobial components from the polymer matrix).

The inventive composition may be solvent cast into a film. The ingredients of the inventive composition are dissolved or at least partially solvated, and thoroughly mixed in a suitable solvent which is then cast on a surface and allowed to evaporate, leaving solids comprising the inventive antimicrobial resin composition.

The invention will be further clarified by the following examples which are exemplary and not intended to limit the scope of the invention.

EXAMPLES

Examples 1 and 2

Samples were prepared using a batch Brabender mixing apparatus in which pelletized polylactic acid (PLA polymer obtained from Nature Works LLC in Minneapolis, Minn. as Polymer 4032 D and 4060 D) was added to the Brabender mixer and blended at 180° C. until the mixing torque stabilized. The other ingredients were then added to the mixer, and the total composition was blended until it appeared homogeneous. The mixture was removed from the Brabender apparatus and was pressed into sheets using a hydraulic press the platens of which were at the 177° C. Samples of the sheets produced from this pressing were tested for microbial activity using Japanese Industrial Standard test number Z 2801:2000 using a Gram-positive bacteria (*Staphylococcus aureus* ATGC #6538) and a Gram-negative bacteria (*Pseudomonas aeruginosa* ATCC #9027). The same test was performed on a control sheet of polylactic acid without the added ingredients. The data from this testing is presented in Table 1 below.

TABLE 1

| Sample | PLA (g) | PML (ml) | BA (g) | DOSS (g) | Microbe Count (cfu/ml) | |
|---|---|---|---|---|---|---|
| | | | | | P. aeruginosa | S. aureus |
| PLA-Control 1 | 55 (4032D) | 0 | 0 | 0 | >$10^7$ | >$10^5$ |
| Example 1 | 55 (4060D) | 5 | 1 | 1 | 0 | 0 |
| Example 2 | 55 (4032D) | 9 | 1 | 0 | 0 | 0 |

PML means propyleneglycol monolaurate antimicrobial component, obtained from Abitec Corp., Columbus, Ohio, as Capmul PG12.
BA means benzoic acid enhancer
DOSS means dioctylsulfosuccinate sodium salt surfactant.
PLA 4032D is semicrystalline polylactic acid, from Natureworks LLC, Minnetonka, Minnesota.
PLA 4060D is amorphous polylactic acid from Natureworks LLC, Minnetonka, Minnesota.

The above data show the effectiveness of the inventive composition in sheet form, in preventing bacteria growth.

Examples 3-19

The aliphatic polyesters used in Examples 1 and 2 were used in these examples. The polyester resin was measured into a glass vial in the weight percentage in Table 2 below. The total sample weight for each example (not including solvent) was 4 grams of solids. Thus, for example, for 90% PLA-3.6 g PLA added, for 80% PLA-3.2 g PLA added, and so on. Next, the antimicrobial component and plasticizer, if present, was added directly into the vial in the percentage shown in Table 2. Approximately 22.5 mL to 23.0 mL of solvent was added to the vial. Polymer 4032D PLA was dissolved in dichloromethane. Polymer 4060D PLA was dissolved in ethyl acetate. The contents were mixed (typically overnight) by placing the vials on a roller until the PLA was completely dissolved. The resulting composition was cast as a wet film onto a silicone release liner by coating to a wet thickness of 300 micrometers using a laboratory coating apparatus. The wet films were allowed to dry at room temperature.

Moisture vapor transmission rate (MVTR) was measured for these samples. MVTR was measured by a method similar to ASTM E-96/E 96M-05 using the water method. A 35 mm diameter sample of 0.025 mm thick material having no perforations was cut. The sample was placed between adhesive coated surfaces of two foil adhesive rings, each having a 2.54 cm diameter hole. The holes of each ring were carefully aligned. Finger pressure was used to form a foil/sample/foil assembly that was flat, wrinkle-free, and had no void areas in the exposed sample.

A 4 oz. (0.14 kg) glass jar was filled half-way with distilled water. The jar was fitted with a screw-on cap having a 3.8 cm diameter hole in the center and with a 4.45 cm diameter rubber washer having a 2.84 cm diameter hole in its center. The rubber washer was placed on the lip of the jar and the foil/sample assembly was placed on the rubber washer. The lid was then screwed loosely on the jar.

The assembly was placed in a chamber at 40+/−1° C. and 20+/−2% relative humidity for four hours to equilibrate. The cap was tightened inside the chamber so that the sample was level with the cap (no bulging) and the rubber washer properly seated.

At the end of four hours, the foil/sample assembly was removed from the chamber and weighed immediately to the nearest 0.01 gram (initial weight $W_1$). The assembly was then returned to the chamber for at least 24-48 hours, after which it was removed and weighed immediately to the nearest 0.01 gram (final weight $W_2$). The MVTR in grams of water vapor transmitted per square meter of sample area in 24 hours was calculated according to the following formula (where "T" refers to exposure time in hours):

$$MVTR=(W_1-W_2)(4.74\times10^4)/T$$

Three measurements of each sample were made. If the samples had identical thicknesses (accurate to 2.5µ), the average value was taken.

A relatively high MVTR is desirable in such materials as wound and surgical dressings. The results are shown in Table 2 below.

TABLE 2

| Example No. | Thickness (μ) | PLA | % PLA | Antimicrobial Component | % Antimicrobial Component | 2nd Antimicrobial Component | % 2nd Antimicrobial Component | Plasticizer | % Plasticizer | 24 hr MVTR (g/sq. m/24 hrs.) | 48 hr MVTR (g/sq. m/24 hrs.) |
|---|---|---|---|---|---|---|---|---|---|---|---|
| 3 | 13 | 4060D | 60 | PGL | 25 | BAC | 5 | PA | 10 | 5005 | 5090 |
| 4 | 18 | 40600 | 60 | PGL | 25 | BAC | 5 | PA | 10 | 5309 | 5348 |
| 5 | 15 | 4060D | 60 | PGL | 25 | BAC | 5 | PA | 10 | 5460 | 5492 |
| 6 | 18 | 4060D | 60 | PGM | 25 | BAC | 5 | PA | 10 | 2048 | 1999 |
| 7 | 25 | 4060D | 60 | PGM | 25 | BAC | 5 | PA | 10 | 1536 | 1443 |
| 8 | 18 | 4060D | 60 | PGM | 25 | BAC | 5 | PA | 10 | 1877 | 1803 |
| 9 | 15 | 4032D | 60 | PGL | 25 | BAC | 5 | PA | 10 | 2598 | 2555 |
| 10 | 28 | 4032D | 60 | PGL | 25 | BAC | 5 | PA | 10 | 3147 | 3133 |
| 11 | 15 | 4032D | 60 | PGL | 25 | BAC | 5 | PA | 10 | 2730 | 2710 |
| 12 | 28 | 4032D | 60 | PGM | 25 | BAC | 5 | PA | 10 | 2294 | 2277 |
| 13 | 15 | 4032D | 60 | PGM | 25 | BAC | 5 | PA | 10 | 2180 | 2174 |
| 14 | 28 | 4060D | 70 | PGM | 25 | BAC | 5 | — | 0 | 1157 | 1072 |
| 15 | 28 | 4060D | 70 | PGL | 25 | BAC | 5 | — | 0 | 1289 | 1267 |
| 16 | 36 | 4060D | 70 | PGL | 25 | BAC | 5 | — | 0 | 815 | 824 |
| 17 | 56 | 4060D | 72 | PGM | 10 | — | 0 | PA | 18 | 533 | 494 |
| 18 | 46 | 4032D | 90 | BAC | 10 | — | 0 | — | 0 | 257 | 247 |
| 19 | 33 | 4060D | 95 | BAC | 5 | — | 0 | — | 0 | 1323 | 1027 |
| Control 2 | 107 | 4060D | 100 | — | 0 | — | 0 | — | 0 | 197 | 178 |

In Table 2:

PA means polyester adipate obtained as Paraplex G50 from CP Hall Company, Bedford Park, Ill.

PGL means polypropylene glycol laurate obtained as Capmul PG 12 from Abitec Corp, Columbus, Ohio.

PGM means polypropylene glycol monocaprylate obtained as Capmul PG8 from Abitec.

BAC means benzalkonium chloride obtained from Sigma Adrich Company, St. Louis, Mo.

The data in Table 2 shows that cast films of the inventive compositions have a beneficial effect on MVTR.

Preparation of Oligomeric Lactic Acid Enhancer and Master Batches:

An oligomeric enhancer was used in Examples 20-31 and was prepared using the following procedure. An 18.9 liter glass reactor(ambient pressure) was filled with 7.6 liters of an 85% lactic acid aqueous solution (City Chemicals) and 7.6 liters of a 70% glycolic acid aqueous solution (Sigma-Aldrich). Reactor temperature was slowly raised to 100° C. after which the water boiled away from the solution leaving only the acid monomers. Reactor temperature was increased to 163° C. initiating, a condensation polymerization of the lactic and glycolic acids. Reaction was allowed to proceed for 24 hours resulting in a random copolymer or oligomer of the two acids with a molecular weight of 1,000-8,000 $M_w$ for one batch and 700-1,000 $M_w$ for another batch.

Pre-compounded pellets used in Examples 20-30 were prepared with a Werner Pfleiderer ZSK-25 twin screw extruder using the following procedure. The extruder had ten zones, each having a barrel section with a channel for circulating heat transfer fluid, and all but the first (feed) section having electrical heating elements. The screw Configurations were helical conveying screw sections, except that kneading sections: were: used in the second half of zone 2, first half of zone 3, all of zone 5, first half of zone 6, all of zone 8 and the first half of zone 9. Extruder vent plugs at zones 5 and 9 were plugged. Pellets of polylactic acid PLA 6251D (Natureworks LLC, Minneapolis, Minn.) were added to the first zone of the extruder at a rate of 3.6 kg/hr. Antimicrobial fatty acid monoester was pumped into the fourth zone of the extruder using a Dynatec S-05 model grid-melter at a fate of 0.5 kg/hr. The grid-melter used a gear pump to meter liquid monoester through transfer tubing into the extruder. The pump and tubing were operated at room temperature when using propylene glycol monolaurate and at 70° C. when using glycerol monolaurate. The oligomeric enhancer described above was heated to 120° C. in a heated tank and gravity fed to a metering pump which delivered it to zone 7 of the extruder at a rate of 0.5 kg/hr. A metering pump was employed at the discharge of the extruder to feed a strand die having a 6.35 mm diameter opening. The extruded strand was cooled in an 2.4 meter long water trough (with continuously fed tap water) and then, at the outlet of the water bath, pelletized using a Conair pelletizer into approximately 6.35 mm length pellets. The extruder screw speed was maintained at 100 RPM and the following barrel temperature profile was used: zone 1—160° C.; zone 2—200° C.; zone 3—177° C.; zones 4 through 9—160° C. The metering pump (melt pump) was electrically heated and adjustable to a temperature set point, set at 177° C., and pump speed was adjusted manually to maintain a pressure of approximately 70-140 N/cm$^2$ (100-200 lbs/in$^2$) to the inlet of the melt pump.

Three masterbatches were prepared having the compositions listed below. The pellets were dried in a forced air resin drier with frequent stirring to prevent agglomeration of the pellets.

Masterbatch #1: 80% PLA 6251D, 10% glycerol monolaurate (GML) & 10% oligomeric enhancer (OLGA).

Masterbatch #2: 80% PLA6251D, 10% propyleneglycolmonolaurate (PML) & 10% oligomeric enhancer (OLGA).

Masterbatch #3: 90% PLA 6251D & 10% glycerol monolaurate (GML).

Examples 20-23

Blown microfiber nonwoven webs were produced from the masterbatches described above using conventional melt blowing equipment. A 31 mm (screw diameter) conical twin screw extruder (C. W. Brabender Instruments, South Hackensack, N.J.) was used to feed a positive displacement gear pump which was used to meter and pressurize the polymer melt. A 25 cm wide drilled orifice melt-blowing die with 8 orifices per cm of width was used. Each orifice was 0.38 mm in diameter. Extruder temperature was 185° C., die temperature was 180° C., air heater temperature was 200° C., and air manifold pressure was 103 kPa. Total polymer flow rate through the die was approximately 3.6 kg/hr. A control sample (C3), was prepared containing no enhancer or antimicrobial additive. For samples having lower than 10% enhancer of antimicrobial additive, additional virgin PLA resin was added to the masterbatch. Characteristics of the nonwoven webs are shown in Table 3 below.

TABLE 3

| Sample | % wt GML | % wt OLGA | Basis Weight (g/m²) | Web thickness (mm) | Effective Fiber Diameter* (μm) |
|---|---|---|---|---|---|
| C3 | 0 | 0 | 92 | 1.7 | 22.8 |
| Example 20 | 10 | 0 | 95 | 1.3 | 20.7 |
| Example 21 | 10 | 10 | 107 | 0.7 | 10.7 |
| Example 22 | 5 | 5 | 94 | 1.1 | 14.9 |
| Example 23 | 2.5 | 2.5 | 95 | 1.4 | 20.1 |

Examples 24-26

Blown microfiber nonwoven webs were produced as in Examples 20-23 except propyleneglycol monolaurate (PML) was used as the antimicrobial component. Characteristics of the nonwoven webs are shown in Table 4 below.

TABLE 4

| Sample | % wt PML | % wt OLGA | Basis Weight (g/m²) | Web thickness (mm) | Effective Fiber Diameter* (μm) |
|---|---|---|---|---|---|
| Example 24 | 10 | 10 | 103 | 0.8 | 12.5 |
| Example 25 | 5 | 5 | 95 | 1.1 | 15.4 |
| Example 26 | 2.5 | 2.5 | 94 | 1.1 | 14.9 |

*Effective Fiber Diameter (in micrometers) was calculated as described by Davies, C.N., "The Separation of Airborne Dust and Particles", Institution of Mechanical Engineers, London Proceedings 1B, 1952.

Examples 20-23 and C3 were tested for tensile strength and stiffness properties. Peak force tensile strength was measured using ah INSTRON Model 5544 universal tensile testing machine using a crosshead speed of 25.4 cm/min with a gauge length of 5.1 cm. The specimen dimensions were 10.2 cm in length. Machine (MD) and cross (CD) directions of the nonwoven webs were tested. The percent elongation of the specimen at peak force was recorded. Ten replicates were tested and averaged for each sample web. Results are shown below in Table 5.

Stiffness properties of the webs were measured using a Gurley bending resistance tester model 4151E (Gurley Precision Instruments, Troy, N.Y.). 3.8 cm long by 2.5 cm wide specimens were cut from the webs, the long direction being in the machine direction of the web. Each specimen was tested by deflecting the specimen in both the MD and CD and calculating the average of both directions of the pendulum deflections. The tester was used to convert the pendulum deflection measurements and machine settings to Gurley stiffness readings in milligrams. Ten replicates were tested and averaged for each sample web. Results are shown below in Table 5.

TABLE 5

| Sample | Peak Force MD (g/cm width) | Elongation MD (%) | Peak Force CD (g/cm width) | Elongation CD (%) | Stiffness (mg) |
|---|---|---|---|---|---|
| C3 | 66 | 15.8 | 93 | 102.3 | 126 |
| Example 20 | 120 | 11.4 | 129 | 90.1 | 100 |
| Example 21 | 813 | 6.8 | 620 | 7.8 | 507 |
| Example 22 | 377 | 2.8 | 375 | 75.8 | 346 |
| Example 23 | 193 | 15.3 | 188 | 81.5 | 113 |

Antimicrobial Testing of Nonwoven Samples

The following test protocol, adapted from AATCC 100-2004 (Assessment of Antibacterial Finishes on Textile Materials), was used to assess antimicrobial properties of the nonwoven webs.

Day 1
1. Start an overnight growth at 37° C., 250 RPM of *Staphtyococcus aureus* (ATCC #6538) and *Pseudomonas aeruginosa* (ATCC#9027) (used in place of *Escherichia coli*) in 10 ml of Trypticase Soy Broth (TSB) (VWR #90000-378) from a fresh streak plate, (prepared from frozen stocks less than two weeks beforehand.)
2. Prepare and autoclave: 2×100 ml of distilled, deionized water with 200 ul TSB in a 100 ml media bottle and one 500 ml of D/E (Dey Engley) Neutralizing Broth (VWR #90004-038) in a 500 ml media bottle; Also, prepare 1000 ml of phosphate buffered solution (PBS): 0.24 g $KH_2PO_4$, 1.44 g $Na_2HPO_4$, 8 g NaCl, 1L $DDH_2O$, adjust pH to 7.0, autoclave 20 mins at 121° C.

Day 2
3. Cut out squares of the test material that are roughly 4×4 cm. For the control material, cut out sterile gauze of the same size with at least 10 layers. Duplicates should be run for both organisms, for each material, thus totaling 4 sample squares for each test material. The sterile gauze control, however, should have 6 squares so that two may be harvested immediately to determine the colony forming units (CPU's) at time zero (t=0). Place all the square cut-outs of the materials into sterile Petri dishes and label accordingly.
4. Transfer 20 ul (microliters) of the *S. aureus* overnight growth culture into one of the sterile 0.2% TSB media bottles, label the bottle and repeat for the *P. aeruginosa* with the second sterile bottle (prepared on day 1.)
5. Shake the dilute inoculum vigorously to obtain a uniform suspension of cells. Inoculate two of each sample with 1 ml of the cell suspension of *S. aureus*. Repeat for *P. aeruginosa* with the remaining two samples of each material. Label the Petri dishes according to the challenge organism. Inoculate the sterile gauze time-zero controls, one for each organism, and set aside.
6. Place all Petri dishes containing inoculated materials, except time zeroes, into a humidity controlled incubator (70-80% relative humidity or higher). Allow 18-24 hours incubation time at 37° C.
7. Prepare one 50 ml BD Falcon centrifuge tube containing 20 ml sterile Difco D/E Neutralizing Broth (NB) for each (t=0) sample. Label accordingly.
8. Using flame-sterilized tweezers, transfer the t=0 samples into the corresponding tube, pushing the material down into the neutralizing broth.

9. Place the tubes containing the NB and material into on ultrasonic bath for 60 s then vortex for 60 s (seconds) (in substitution of the stomacher) to release the cells from the materials into the NB.
10. Pipette 200 μl of the supernatant NB broth from each falcon tube into the first well of a 96-well plate. Pipette 180 μl of sterile PBS (phosphate buffered solution) into wells 2-6.
11. Make 10-fold serial dilutions by pipetting 20 μl from well 1 to well 2, then from well 2 to 3, from well 3 to 4, from well 4 to 5 and from well 5 to 6.
12. Using a permanent marker, divide two TSB agar plates into thirds, and label the sections 0, 1 & 2 on the first plate and 3, 4 & 5 on the second. Make a set for each sample.
13. Using an automatic pipettor, remove the liquid from the highest dilution ($10^{-5}$) and make ten 10 μl aliquots on the section of the plate labeled with the corresponding dilution (5). Repeat for dilutions $10^{-4}$ through $10^0$, plating on sections 4 through 0. Incubate overnight right-side up at 37° C. Reference for drop-dilution method:

Day 3

14. Remove the Petri dishes containing test samples from the incubator and repeat steps 7 through 13 for these materials.
15. Remove the t=0 agar plates with dilution series from the incubator. Count and average the dilution containing between 5 and 60 colony forming units (CPU's). This will be the average CFU per 10 ul. Multiply by 100 to obtain CFU per ml then multiply this number by 20 ml to determine CFU per sample. If CFU's are detected, the sensitivity limit of this test is assigned: 200 CFU/sample. Calculate the log reduction by taking the log base 10 of the quotient of CFU per sample at time zero divided by the CFU per sample at harvest.

Day 4

16. Repeat step 15 for the agar plates containing the dilution series for the test materials and controls.

TABLE 6

(AATCC 100-2004 Antibacterial testing using *Staphlyococcus aureus*)

| Sample | CFU/ml | CFU/sample |
|---|---|---|
| t = 0 | 80000 | 1600000 |
| C3 | 42000 | 840000 |
| 20 | 0 | 0 |
| 21 | 0 | 0 |
| 22 | 0 | 0 |
| 23 | 230 | 4600 |

Values of 0 in Tables 6-11 indicate results which were below the detection limit of the test: approximately 200 CFU/sample.

TABLE 7

(AATCC 100-2004 Antibacterial testing usinig *Pseudomonas aeruginosa*)

| Sample | CFU/ml | CFU/sample |
|---|---|---|
| t = 0 | 34000 | 680000 |
| C3 | 2600000 | 52000000 |
| 20 | 2200 | 4000 |
| 21 | 0 | 0 |
| 22 | 0 | 0 |
| 23 | 330000 | 6600000 |

TABLE 8

(Log Reduction vs t = 0)

| Sample | *Staphlyococcus aureus* | *Pseudomonas aeruginosa* |
|---|---|---|
| C3 | 0.5 | −1.6 |
| 20 | 3.9 | 1.2 |
| 21 | 3.9 | 3.5 |
| 22 | 3.9 | 3.5 |
| 23 | 2.5 | −1.0 |

TABLE 9

(AATCC 100-2004 Antibacterial testing using *Staphlyococcus aureus*)

| Sample | CFU/ml | CFU/sample |
|---|---|---|
| t = 0 | 130000 | 2600000 |
| C3 | 42000 | 840000 |
| 24 | 0 | 0 |
| 25 | 0 | 0 |
| 26 | 15 | 300 |

TABLE 10

(AATCC 100-2004 Antibacterial testing using *Pseudomonas aeruginosa*)

| Sample | CFU/ml | CFU/sample |
|---|---|---|
| t = 0 | 70000 | 1400000 |
| C3 | 2600000 | 52000000 |
| 24 | 0 | 0 |
| 25 | 0 | 0 |
| 26 | 25 | 500 |

TABLE 11

(Log Reduction vs t = 0)

| Sample | *Staphlyococcus aureus* | *Pseudomonas aeruginosa* |
|---|---|---|
| C3 | 0.5 | −1.6 |
| 24 | 4.1 | 3.8 |
| 25 | 4.1 | 3.8 |
| 26 | 3.9 | 3.4 |

Examples 27-29

Antimicrobial extruded films were produced using the following procedure. The corotating twin screw extruder, used to compound masterbatch pellets described above, was used to melt, blend and feed the polymer and additives. The screw sections were set up with kneading blocks at zones 2, 4 and 6. The extruder had 9 temperature controllable barrel zones, with an input port for dry pellets at zone 1 and liquid injection ports at zones 3 and 5. A weight loss gravimetric feeder (K-tron, Pitman N.J.) was used to feed dry pellets at zone 1. 4032D semicrystalline polylactic acid (PLA) (Natureworks LLC) pellets were first dried overnight at 60° C. in a resin dryer to remove water. A grid-melter, (Dynatec, Hendersonville Tenn.) was used to melt and feed propylene glycol inonolaurate (PML), (Capmul PG-12, Abitec, Janesville Wis.), into zone 3 of the extruder. A metering pump (Zenith pump, Sanford, N.C.). was used to feed oligomeric enhancer (OLGA) into zone 5 of the extruder. The enhancer was gravity fed from a heated pot directly above the pump.

The melt from the extruder was fed to a metering pump, and then into a 15.24 cm wide coat-hanger die. The extrudate was extruded horizontally onto a 15.24 cm diameter temperature controlled roll. The resulting web was pulled around the roll at a 270° wrap angle. The web was then wrapped around a Second 15.2 cm diameter temperature controlled roll at a 180° wrap. The web was then pulled with a nip and wrapped onto a core. Film caliper was measured with a micrometer to the nearest 2.5 microns. Film caliper was maintained to +/−15 microns using disadjustment bolts. The compositions of the films are shown below in Table 12.

TABLE 12

| Sample | PLA % | PML % | OLGA % |
|---|---|---|---|
| C4 | 100 | 0 | 0 |
| 27 | 80 | 10 | 10 |
| 28 | 90 | 10 | 0 |
| 29 | 90 | 0 | 10 |

Example 30

Extruded films were prepared as in Examples 27-29 except polycaprolactone (PGL, type FB 100, Solvay Chemicals, Houston Tex.) was used as the base polymer. The compositions of the films are shown below in Table 13.

TABLE 13

| Sample | PCL % | PML % | OLGA % |
|---|---|---|---|
| C5 | 100 | 0 | 0 |
| 30 | 90 | 5 | 5 |

Antimicrobial Testing of Film Samples

The following test protocol, adapted from JIS Z2801 (Japanese Industrial Standard—Test for Antimicrobial Activity), was used to assess the antimicrobial properties of extruded or pressed films.

Day 1

1. Start overnight growth cultures at 37° C., 250 RPM for *P. aeruginosa* (ATCC #9027) and *S. aureus* (ATCC #6538) via stem-loop inoculation from freshly-streaked agar plates (less than two weeks old) into a sterile culture tube containing 10 ml of Trypticase Soy Broth (VWR #90000-378). Allow to grow for 18-24 hours before use.
2. Prepare and autoclave 500 ml of D/E Neutralizing Broth (VWR cat #90004-038) at 121° C. for 15 minutes (Used as an alternative to SCDLP broth, defined in JISZ2801 protocol)
3. Prepare and autoclave 2×100 ml 0.2% TSB in distilled, deionized water at 121° C. for 15 minutes.

Day 2

4. Cut out four 4×4 cm pieces of each test material and polyethylene terephthalate control (3-4 mil thickness). Cut out two extra 4×4 cm pieces of the polyester film control to use for determining 'time zero' counts. Two of the four pieces from each material will be inoculated with *S. aureus*, and the other two with *P. aeruginosa*.
5. Place the materials into sterile Petri dishes labeled for the material, the replicate number and the organism. There should be two extra controls. Designate one for *S. aureus* and the other for *P. aeruginosa* and label them both "t=0". To sterilize, wipe both sides of each material using a paper towel moistened with isopropanol of 70% ethanol and allow to dry.
6. Cut out 2×2 cm pieces of covering film (polyester, 3-4 mil thick) for each 4×4 cm piece of test material, set aside. To sterilize, wipe the coverslips with isopropanol or 70% ethanol and allow to dry. The purpose of these coverslips is to increase the surface area contact between the material and the inoculum by sandwiching the inoculum between it and the material surface.
7. Prepare the inoculum for both organisms by pipetting 20 µl from the overnight Culture into the 100 ml of 0.2% TSB prepared on Day 1 for a final suspension of about $10^6$ cells/ml. Label according to the organism.
8. Pipette 400 µl of the cell suspension onto the material in the Petri dishes. Place covering film over inoculum. Ensure labeling accuracy regarding the organism.
9. Set aside the two t=0 Petri dishes, then place the others in an environment-controlled incubator at 37° C., 70-80% relative humidity for 18-24 hours.
10. Using flame-sterilized tweezers, remove the inoculated material from the t=0, *S. aureus* Petri dish. Place it into a labeled 50 ml Falcon tube containing 10 ml of D/E Neutralizing broth and place in an ultrasonic bath for 1 min. Remove samples from ultrasonic bath, then vortex for 1 min (used in place of the stomacher.) Repeat for the t=0, *P. aeruginosa* material.
11. Pipette 200 µl of the broth from the falcon tube into the first well of a 96-well plate. Pipette 180 µl of sterile. PBS into wells 2-6.
12. Make 10-fold serial dilutions by pipetting 20 µl from well 1 to well 2, then from well 2 to 3, from well 3 to 4, from well 4 to 5 and from well 5 to 6.
13. Using a permanent marker, divide two TSB agar plates into thirds, and label the sections 0, 1 & 2 on the first plate and 3, 4 & 5 on the second.
14. Using an automatic pipettor, remove the liquid from the highest dilution ($10^{-5}$) and make ten 10 µl aliquots on the section of the plate labeled with the corresponding dilution (5). Repeat for dilutions $10^{-4}$ through $10^0$, plating on sections 4 through 0. Incubate overnight right-side up at 37°.

Day 3

15. Count, record, and average the number of colony forming units (CFU's) in each section of the t=0 dilution plates. Determine the CFU/ml and standard deviation of the CFU/ml then compile the most reliable counts from each dilution series and average the CFU/ml for each species on each material. Multiply this number by 10 to determine the CFU/sample. If a count is zero, then it is assigned the sensitivity limit of this test; 100 CFU/sample. Calculate the log reduction by taking the log base 10 of the quotient of CFU per sample at time zero over the CFU per sample at harvest.
16. Remove the inoculated materials from the incubator and harvest the inoculum from each sample by following the, same steps (10-14) used in harvesting the t=0.

Day 4
17. Repeat step 15.
Antimicrobial properties of the extruded films are shown in Tables 14, 15 and 16 below.

TABLE 14

(Antibacterial testing using *Staphlyococcus aureus*)

| Sample | CFU/ml | CFU/sample |
|---|---|---|
| t = 0 | 39000 | 390000 |
| C4 | 4950 | 49500 |
| 27 | 0 | 0 |
| 28 | 1150 | 11500 |
| 29 | 4500 | 45000 |
| C5 | 490000 | 4900000 |
| 30 | 0 | 0 |

Values of 0 in Tables 14-15 indicate results below the detection limit of the test: approximately 100 CFU/sample.

These results show that the addition of the PML (ex. 28) reduces the Gram positive bacteria counts over the control (C4). The addition of OLGA had little antimicrobial effect (Ex. 29). The addition of both PML and OLGA however, produced a composition with exceptional antimicrobial activity reducing the bacterial count to none detectable.

TABLE 15

(Antibacterial testing using *Pseudomonas aeruginosa*)

| Sample | CFU/ml | CFU/sample |
|---|---|---|
| t = 0 | 72000 | 720000 |
| C4 | 1650000 | 16500000 |
| 27 | 0 | 0 |
| 28 | 8000000 | 80000000 |
| 29 | 1262500 | 12625000 |
| C5 | 3700000 | 37000000 |
| 30 | 0 | 0 |

These results show that the addition of the PML (ex. 28) did not reduce Gram negative bacteria counts over the control (C4). The addition, of OLGA had little antimicrobial effect (Ex. 29). The addition of both PML and OLGA (Examples 27 and 30) produced a composition with exceptional antimicrobial activity reducing the bacteria to none detectable.

TABLE 16

(Log reduction versus t = 0)

| Sample | *Staphlyococcus aureus* | *Pseudodnonas aeruginosa* |
|---|---|---|
| C4 | −0.1 | −1.4 |
| 27 | 3.6 | 3.9 |
| 28 | 1.5 | −2.0 |
| 29 | 0.9 | −1.2 |
| C5 | −1.1 | −1.7 |
| 30 | 3.6 | 3.9 |

Table 16 was calculated by taking the log-base-10 of the quotient of the time-zero CFU/sample count by the final CFU/sample count. The log-reduction for counts of zero were calculated by dividing the time-zero CFU/sample by the detection limit (100 CFU/sample).

Example 31

An adhesive tape dispenser was injection molded using a single cavity, single hot gate, mold maintained at a temperature of 70° C. A resin composition of 80% 3051D PLA (Natureworks LLC), 10% PML and 10% OLGA was used. The weight of the finished molded product was 24 grams. An Engel ES 100 TL molding machine was used equipped with a 25 mm 28:1 L/D injection molding screw, delivering a maximum shot size of 45 grams, a maximum injection rate of 67 cm$^3$/sec at a maximum injection pressure of 16 kN/cm$^2$. Melt temperature of the injected resin was approximately 204° C.

Data have shown that PML (propylene glycol monolaurate) and OLGA (oligomeric enhancer reaction product of lactic acid and glycolic acid described above) when used in combination with polylactic acid or polycaprolactone tend to increase the wetting ability (decreased water contact angle) of articles made from these polymers. Such increased wetting can be an advantage in such applications as surgical drapes.

While certain representative embodiments and details have been discussed above for purposes of illustrating the invention, various modifications may be made in this invention without departing from its true scope, which is indicated by the following claims.

What is claimed is:

1. A melt-processed material comprising:
  a) at least 50 percent by weight of a thermoplastic aliphatic polyester;
  b) an antimicrobial component incorporated within the thermoplastic aliphatic polyester, wherein the antimicrobial component is selected from the group consisting of: cationic antimicrobial amine compounds; ($C_7$-$C_{22}$) saturated fatty acid esters of a polyhydric alcohol, ($C_8$-$C_{22}$) unsaturated fatty acid esters of a polyhydric alcohol, ($C_7$-$C_{22}$) saturated fatty ethers of a polyhydric alcohol, ($C_8$-$C_{22}$) unsaturated fatty ethers of a polyhydric alcohol, ($C_2$-$C_8$) hydroxy acid esters of ($C_7$-$C_{22}$) alcohols, alkoxylated derivatives thereof, and combinations thereof, wherein the alkoxylated derivatives have less than 5 moles of alkoxide group per mole of polyhydric alcohol or per mole of hydroxycarboxylic acid and wherein the alkoxylated derivatives are ethoxylated derivatives or propoxylated derivatives or mixtures thereof; with the proviso that for polyhydric alcohols other than sucrose, the esters comprise monoesters and the ethers comprise monoethers, and for sucrose the esters comprise monoesters, diesters, or combinations thereof, and the ethers comprise monoethers, diethers, or mixtures thereof, wherein the antimicrobial component is present in an amount greater than 1 percent by weight of the thermoplastic aliphatic polyester; and
  c) an enhancer selected from the group consisting of beta-hydroxy acids, chelating agents other than beta-hydroxy acids, ($C_2$-$C_6$) saturated or unsaturated alkyl carboxylic acids, ($C_6$-$C_{16}$) aryl carboxylic acids, ($C_6$-$C_{16}$) aralkyl carboxylic acids, ($C_6$-$C_{12}$) alkaryl carboxylic acids, phenolic compounds, ($C_1$-$C_{10}$) alkyl alcohols, ether glycols, oligomeric polyesters having a weight average molecular weight of less than 10,000 daltons that degrade to release at least one beta-hydroxy acids, and mixtures thereof in an amount greater than 0.1 percent by weight of the thermoplastic aliphatic polyester, provided that, if the enhancer comprises ether glycols or phenolic compounds, the ether glycols or phenolic compounds are present in an amount greater than 0.5 percent by weight of the thermoplastic aliphatic polyester; wherein the enhancer is present in a total amount of no greater than 10 wt-%, based on the total weight of the melt-processed material;

provided that, if the antimicrobial component is selected from ($C_7$-$C_{22}$) saturated fatty acid esters of a polyhydric alcohol, ($C_8$-$C_{22}$) unsaturated fatty acid esters of a polyhydric alcohol, or ethoxylated and/or propoxylated derivatives thereof, the purity of the antimicrobial component exceeds 85 percent by weight monoester;

wherein the melt-processed material exhibits enhanced antimicrobial activity relative to a similar melt-processed material excluding the enhancer, wherein enhanced microbial activity is selected from the group consisting of increased level of kill, increased speed of kill, increased spectrum of kill, and combinations thereof; and wherein the melt-processed material is in the form of fibers, film, or foam.

2. The material of claim 1, wherein the antimicrobial component b) is a plasticizer, to form a plasticized aliphatic polyester.

3. The material of claim 1, further comprising a plasticizer distinct from the antimicrobial component b) and the enhancer component c).

4. The material of claim 2, wherein the plasticized aliphatic polyester has a lower melt processing temperature than the aliphatic polyester alone.

5. The material of claim 1, further comprising a surfactant distinct from the antimicrobial component b).

6. The material of claim 5, wherein the surfactant is selected from the group consisting of sulfate, sulfonate, phosphonate, phosphate, poloxamer, alkyl lactate, carboxylate, cationic surfactants, zwitterionic surfactants, and combinations thereof.

7. The material of claim 5, wherein the surfactant is selected from ($C_8$-$C_{22}$) alkyl sulfate salts, di($C_8$-$C_{18}$)sulfosuccinate salts, $C_8$-$C_{22}$ alkyl sarcosinate, and combinations thereof.

8. The material of claim 1, wherein the thermoplastic aliphatic polyester is selected from the group consisting of polybutylenesuccinate homopolymer, polybutylene adipate homopolymer, polybutyleneadipate-succinate copolymer, polyethylenesuccinate-adipate copolymer, polyethylene glycol succinate and polyethylene adipate homopolymer, poly (lactide), poly(glycolide), poly(lactide-co-glycolide), poly (L-lactide-co-trimethylene carbonate), poly(dioxanone), poly(butylene succinate), poly(butylene adipate), and mixtures thereof.

9. The material of claim 1, wherein the thermoplastic aliphatic polyester is polylactic acid.

10. The material of claim 1, wherein the thermoplastic aliphatic polyester is semicrystalline.

11. The material of claim 1, wherein the antimicrobial component b) is present in an amount greater than 5 percent by weight of the aliphatic polyester.

12. The material of claim 1, wherein the antimicrobial component b) is present in an amount greater than 13 percent by weight of the aliphatic polyester.

13. The material of claim 1, wherein the antimicrobial component b) is present in an amount greater than 20 percent by weight of the aliphatic polyester.

14. The material of claim 1, wherein the antimicrobial component b) is selected from the group consisting of:
($C_7$-$C_{22}$) saturated fatty acid esters of a polyhydric alcohol selected from ($C_7$-$C_{12}$) propylene glycol monoesters and glycerol monoesters;

cationic antimicrobial amine compounds selected from quaternary ammonium compounds, protonated tertiary amines, benzalkonium halides and alkyl substituted derivatives thereof, di-long chain alkyl ($C_8$-$C_{18}$) quaternary ammonium compounds, cetylpyridinium halides benzethonium halides, alkyl substituted benzethonium halides, and octenidine; and
combinations thereof.

15. The material of claim 1, wherein the antimicrobial component b) is selected from the group consisting of:
($C_7$-$C_{22}$) saturated fatty acid esters of a polyhydric alcohol selected from propyleneglycol monolaurate, propyleneglycol monocaprylate, and glycerol monolaurate;
cationic antimicrobial amine compounds selected from polymeric biguanides, polyhexamethylene biguanide, bisbiguanides, and lauroylethylarginate; and
combinations thereof.

16. The material of claim 1, wherein the enhancer c) is selected from the group consisting of:
($C_6$-$C_{16}$) aryl carboxylic acids selected from benzoic acid;
beta-hydroxy acids selected from salicylic acid;
chelating agents selected from adipic acid, succinic acid, sorbic acid, ethylenediaminetetraacetic acid and partial or fully neutralized salts thereof;
phenolic compounds selected from butylatedhydroxytoluene, butylatedhydroxyanisole, methyl paraben, ethyl paraben, propyl paraben, and butyl paraben; and
mixtures thereof.

17. The material of claim 1, wherein the antimicrobial component b) is present at a concentration of less than 35 wt. %, based on the weight of the melt-processed material.

18. The material of claim 1, which is in the form of fibers having an effective fiber diameter of 20.7 microns or less.

19. A melt-processed material comprising:
a) at least 50 percent by weight of a thermoplastic aliphatic polyester;
b) an antimicrobial component incorporated within the thermoplastic aliphatic polyester, wherein the antimicrobial component is selected from the group consisting of: cationic antimicrobial amine compounds; ($C_7$-$C_{22}$) saturated fatty acid esters of a polyhydric alcohol, ($C_8$-$C_{22}$) unsaturated fatty acid esters of a polyhydric alcohol, ($C_7$-$C_{22}$) saturated fatty ethers of a polyhydric alcohol, ($C_8$-$C_{22}$) unsaturated fatty ethers of a polyhydric alcohol, ($C_2$-$C_8$) hydroxy acid esters of ($C_7$-$C_{22}$) alcohols, alkoxylated derivatives thereof, and combinations thereof, wherein the alkoxylated derivatives have less than 5 moles of alkoxide group per mole of polyhydric alcohol or per mole of hydroxycarboxylic acid and wherein the alkoxylated derivatives are ethoxylated derivatives or propoxylated derivatives or mixtures thereof; with the proviso that for polyhydric alcohols other than sucrose, the esters comprise monoesters and the ethers comprise monoethers, and for sucrose the esters comprise monoesters, diesters, or combinations thereof, and the ethers comprise monoethers, diethers, or mixtures thereof, wherein the antimicrobial component is present in an amount greater than 1 percent by weight of the thermoplastic aliphatic polyester;
c) an enhancer selected from the group consisting of alpha-hydroxy acids, beta-hydroxy acids, chelating agents other than alpha-hydroxy acids and beta-hydroxy acids, ($C_2$-$C_6$) saturated or unsaturated alkyl carboxylic acids, ($C_6$-$C_{16}$) aryl carboxylic acids, ($C_6$-$C_{16}$) aralky carboxylic acids, ($C_6$-$C_{12}$) alkaryl carboxylic acids, phenolic compounds, ($C_1$-$C_{10}$) alkyl alcohols, ether glycols, and mixtures thereof in an amount greater than 0.1 percent by weight of the thermoplastic aliphatic polyester, provided that, if the enhancer comprises ether glycols or phenolic compounds, the ether glycols or phenolic compounds are present in an amount greater than 0.5 percent by weight of the thermoplastic aliphatic polyester; wherein the enhancer is present in a total amount of no greater than 10 wt-%, based on the total weight of the melt-processed material; and d) a surfactant distinct from the antimicrobial component b), wherein the surfactant is incorporated within the thermoplastic aliphatic polyester;

provided that, if the antimicrobial component is selected from ($C_7$-$C_{22}$) saturated fatty acid esters of a polyhydric alcohol, ($C_8$-$C_{22}$) unsaturated fatty acid esters of a polyhydric alcohol, or ethoxylated and/or propoxylated derivatives thereof, the purity of the antimicrobial component exceeds 85 percent by weight monoester;

wherein the melt-processed material exhibits enhanced antimicrobial activity relative to a similar melt-processed material excluding the enhancer, wherein enhanced microbial activity is selected from the group consisting of increased level of kill, increased speed of kill, increased spectrum of kill, and combinations thereof; and wherein the melt-processed material is in the form of fibers, film, or foam.

20. The material of claim 19, wherein the surfactant is selected from the group consisting of sulfate, sulfonate, phosphonate, phosphate, poloxamer, alkyl lactate, carboxylate, cationic surfactants, zwitterionic surfactants, and combinations thereof.

21. The material of claim 20, wherein the surfactant is selected from ($C_8$-$C_{22}$) alkyl sulfate salts, di($C_8$-$C_{18}$)sulfosuccinate salts, $C_8$-$C_{22}$ alkyl sarcosinate, and combinations thereof.

22. The material of claim 19, which is in the form of fibers having an effective fiber diameter of 20.7 microns or less.

23. A melt-processed material comprising:
a) at least 50 percent by weight of a thermoplastic aliphatic polyester having a molecular weight of at least 50,000 daltons;
b) an antimicrobial component incorporated within the thermoplastic aliphatic polyester, wherein the antimicrobial component comprises a cationic antimicrobial amine compound; and
c) an antimicrobial enhancer in a total amount of no greater than 10 wt-%, based on the total weight of the melt-processed material;
wherein the melt-processed material is in the form of fibers, film, or foam.

24. The material of claim 23, which is in the form of fibers having an effective fiber diameter of 20.7 microns or less.

25. The material of claim 23, wherein the antimicrobial component b) is present at a concentration of less than 35 wt. %, based on the weight of the melt-processed material.

26. The material of claim 24, further comprising a surfactant in or on the fibers.

27. A melt-processed material comprising:
a) at least 50 percent by weight of a thermoplastic aliphatic polyester having a molecular weight of at least 50,000 daltons;
b) an antimicrobial component incorporated within the thermoplastic aliphatic polyester, wherein the antimicrobial component is lipophilic and has a solubility in water of no greater than 1.0 gram per 100 grams (1.0 g/100 g) deionized water; and
c) an antimicrobial enhancer in a total amount of no greater than 10 wt-%, based on the total weight of the melt-processed material;
wherein the melt-processed material is in the form of fibers, film, or foam.

28. The material of claim 27, wherein the antimicrobial component has a solubility in water of no greater than 0.5 g/100 g deionized water.

29. The material of claim 28, wherein the antimicrobial component has a solubility in water of no greater than 0.25 g/100 g deionized water.

30. The material of claim 29, wherein the antimicrobial component has a solubility in water of no greater than 0.10 g/100 g deionized water.

31. The material of claim 28, which is in the form of fibers having an effective fiber diameter of 20.7 microns or less.

32. The material of claim 27, wherein the antimicrobial component b) is present at a concentration of less than 35 wt. %, based on the weight of the melt-processed material.

33. The material of claim 31, further comprising a surfactant in or on the fibers.

34. Fibers having an effective fiber diameter of 20.7 microns or less, wherein the fibers comprise a melt processed material comprising:
a) at least 50 percent by weight of a thermoplastic aliphatic polyester within the fibers;
b) an antimicrobial component incorporated within the thermoplastic aliphatic polyester, wherein the antimicrobial component is selected from the group consisting of: cationic antimicrobial amine compounds; ($C_7$-$C_{22}$) saturated fatty acid esters of a polyhydric alcohol, ($C_8$-$C_{22}$) unsaturated fatty acid esters of a polyhydric alcohol, ($C_7$-$C_{22}$) saturated fatty ethers of a polyhydric alcohol, ($C_8$-$C_{22}$) unsaturated fatty ethers of a polyhydric alcohol, ($C_2$-$C_8$) hydroxy acid esters of ($C_7$-$C_{22}$) alcohols, alkoxylated derivatives thereof, and combinations thereof, wherein the alkoxylated derivatives have less than 5 moles of alkoxide group per mole of polyhydric alcohol or per mole of hydroxycarboxylic acid and wherein the alkoxylated derivatives are ethoxylated derivatives or propoxylated derivatives or mixtures thereof; with the proviso that for polyhydric alcohols other than sucrose, the esters comprise monoesters and the ethers comprise monoethers, and for sucrose the esters comprise monoesters, diesters, or combinations thereof, and the ethers comprise monoethers, diethers, or mixtures thereof, wherein the antimicrobial component is present in an amount greater than 1 percent by weight of the thermoplastic aliphatic polyester;
c) an enhancer in or on the fibers, wherein the enhancer is selected from the group consisting of alpha-hydroxy acids, beta-hydroxy acids, chelating agents other than alpha-hydroxy acids and beta-hydroxy acids, ($C_2$-$C_6$) saturated or unsaturated alkyl carboxylic acids, ($C_6$-$C_{16}$) aryl carboxylic acids, ($C_6$-$C_{16}$) aralkyl carboxylic acids, ($C_6$-$C_{12}$) alkaryl carboxylic acids, phenolic compounds, ($C_1$-$C_{10}$) alkyl alcohols, ether glycols, oligomeric polyesters having a weight average molecular weight of less than 10,000 daltons that degrade to release at least one of alpha-hydroxy acids and beta-hydroxy acids, and mixtures thereof in an amount greater than 0.1 percent by weight of the thermoplastic aliphatic polyester, provided that, if the enhancer comprises ether glycols or phenolic compounds, the ether glycols or phenolic compounds are present in an amount greater than 0.5 percent by weight of the thermoplastic aliphatic polyester;

wherein the enhancer is present in a total amount of no greater than 10 wt-%, based on the total weight of the fibers; and d) a surfactant distinct from the antimicrobial component b) in the fibers;

provided that, if the antimicrobial component is selected from ($C_7$-$C_{22}$) saturated fatty acid esters of a polyhydric alcohol, ($C_8$-$C_{22}$) unsaturated fatty acid esters of a polyhydric alcohol, or ethoxylated and/or propoxylated derivatives thereof, the purity of the antimicrobial component exceeds 85 percent by weight monoester;

wherein the melt-processed material exhibits enhanced antimicrobial activity relative to a similar melt-processed material excluding the enhancer, wherein enhanced microbial activity is selected from the group consisting of increased level of kill, increased speed of kill, increased spectrum of kill, and combinations thereof.

35. An article comprised of the material of claim 1, said article being selected from polymeric sheet, polymeric fibers, woven webs, nonwoven webs, polymeric foams thermal or adhesive laminates, layered materials and combinations thereof.

36. A surgical drape comprising nonwoven web comprising the material of claim 1.

37. A surgical gown comprising nonwoven web comprising the material of claim 1.

38. A process for making an antimicrobial melt-processed material, the process comprising:
   i) providing the components of claim 1; and
   ii) mixing the aliphatic polyester of a) in melt form with the antimicrobial component of b) and the enhancer of c) to form an antimicrobial material.

* * * * *

UNITED STATES PATENT AND TRADEMARK OFFICE
CERTIFICATE OF CORRECTION

| | | |
|---|---|---|
| PATENT NO. | : 9,555,167 B2 | |
| APPLICATION NO. | : 11/609237 | |
| DATED | : January 31, 2017 | |
| INVENTOR(S) | : Matthew J. Schmid et al. | |

It is certified that error appears in the above-identified patent and that said Letters Patent is hereby corrected as shown below:

In the Specification

Column 1,
Line 17, "poly (lactic acid)," should read --poly(lactic acid),--.
Line 29, "spunbound" should read --spunbond--.
Line 38, "Nos." should read --No.--.

Column 2,
Line 20, "alcohols;" should read --alcohols,--.

Column 3,
Line 53, "implanted/in" should read --implanted in--.
Line 63, "sufficient;" should read --sufficient--.

Column 4,
Line 8, "Z28801:2000" should read --Z 2801:2000--.
Line 42, "ph" should read --pH--.
Line 47, "μg/100 μg" should read --μg/100g--.

Column 5,
Lines 24-25, "poly(hydroxyalkanoates)j" should read --poly(hydroxyalkanoates)--.
Line 48, "daltons," should read --daltons.--.

Column 6,
Line 28, "catenary" should read --caternary--.
Line 33, "1,12dicarboxydodecane," should read --1,12-dicarboxydodecane,--.
Line 33, "glutartic" should read --glutaric--.
Lines 53-54, "poly(lactide);" should read --poly(lactide),--.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*

Column 7,
Line 23, "Tsujiet." should read --Tsuji et.--.
Line 29, "acid;" should read --acid,--.
Line 55, "*Chemosphere.*" should read --*Chemosphere,*--.
Line 63, "(e;g" should read --(e.g.--.

Column 8,
Line 20, "If" should read --It--.
Line 24, "con" should read --can--.
Line 26, "arc" should read --are--.
Line 39, "0.1.0 wt." should read --0.10 wt.--.
Line 40, "Order" should read --order--.
Line 41, "to,give" should read --to give--.
Line 47, "%,5" should read --%, 5--.
Line 57, "(C7-C12)saturated" should read --(C7-C12 saturated--.
Lines 58-59, "(C8-C12)saturated" should read --(C8-C12) saturated--.

Column 9,
Line 1, "arc" should read --are--.
Line 26, "hydroxy 1" should read --hydroxyl--.
Line 41, "*Protection.*" should read --*Protection,*--.
Line 42, "*Safety.*" should read --*Safety,*--.
Line 46, "ethylarginatc" should read --ethylarginate--.

Column 10,
Line 20, "(C7-C12)saturated" should read --(C7-C12) saturated--.
Line 57, "include," should read --include--.

Column 11,
Line 2, "ho" should read --no--.
Line 27, "ho" should read --no--.
Line 40, "(C7-C14)saturated:" should read --(C7-C14) saturated--.
Line 52, "groups," should read --groups--.

Column 12,
Line 7, "of" should read --or--.
Line 13, "lacate," should read --lactate,--.
Line 36, "ate" should read --are--.
Line 48, "quarternary" should read --quaternary--.
Line 50, "groups," should read --groups--.
Line 59, "$R^9$or" should read --$R^9$ or--.
Line 59, "C8 -C18" should read --C8-C18--.

Column 13,

Line 2, "behzethonium" should read --benzethonium--.
Lines 8-9, "benzalkoniumchloride comprising40%" should read --benzalkonium chloride comprising 40%--.
Line 12, "oh" should read --on--.
Line 14, "Or" should read --or--.
Line 27, "of" should read --or--.

Column 14,
Line 4, "arc" should read --are--.
Line 40, "*Psuedomonas*" should read --*Pseudomonas*--.

Column 15,
Line 3, "acid-groups" should read --acid groups--.
Line 16, "wt; %," should read --wt. %,--.
Line 29, "of." should read --of--.
Line 45, "add," should read --acid,--.
Lines 46-47, "hydroxycaprylic:" should read --hydroxycaprylic--.
Line 57, "invention," should read --invention--.
Line 64, "result" should read --result.--.

Column 16,
Line 2, "oh" should read --on--.
Line 29, "are/not" should read --are not--.
Line 47, "surface," should read --surface--.
Line 50, "most," should read --most--.
Line 54, "or" should read --or at most 1:1.--.

Column 17,
Line 25, "groups" should read --groups;--.
Line 41, "prefefably" should read --preferably--.
Line 67, "Siderophpres" should read --Siderophores--.

Column 18,
Line 1, "enterochlin," should read --enterochelin,--.
Line 2, "aerobaetin." should read --aerobatin.--.
Line 17, "1.0:1" should read --10:1--.
Line 31, "of" should read --or--.
Line 60, "oh" should read --on--.
Line 64, "wt-%,based" should read --wt-%, based--.

Column 19,
Line 4, "tobe" should read --to be--.

CERTIFICATE OF CORRECTION (continued)
U.S. Pat. No. 9,555,167 B2

Line 9, "me" should read --the--.
Line 34, "2 wt;" should read --2 wt.--.
Line 41, "0.05 wt:" should read --0.05 wt.--.
Line 67, "and," should read --and--.

Column 20,
Line 30, "used," should read --used--.
Line 45, "hot" should read --not--.
Line 59, "active," should read --active.--.

Column 21,
Line 15, "sarconsinate," should read --sarcosinate,--.
Line 33, "0.5 wt.," should read --0.5 wt.--.
Line 43, "imidazoline," should read --imidazoline--.
Line 57, "aralklyl" should read --aralkyl--.
Line 66, "of" should read --or--.

Column 22,
Line 18, "sufonates," should read --sulfonates,--.
Line 61, "LANTHANOL" should read --LATHANOL--.

Column 23,
Line 19, "Parsipanny," should read --Parsippany,--.
Line 27, "$R^{29}-(C(O)-NH)_a-R^{30}-N^+(R^{3l})_2-R^{32}-COO^-$," should read --$R^{29}-(C(O)-NH)_a-R^{30}-N^+(R^{31})_2-R^{32}-COO^-$,--.
Line 39, "arc" should read --are--.
Line 41, "atoms,or" should read --atoms, or--.
Line 65, "$R^{29}-(C(O)-NH)_a-R^{30}-N^+(R^{3l})_2-R^{32}-SO_3^-$," should read --$R^{29}-(C(O)-NH)_a-R^{30}-N^+(R^{31})_2-R^{32}-SO_3^-$,--.

Column 24,
Line 5, "carboxy late" should read --carboxylate--.
Line 17, "above:" should read --above.--.
Line 29, "trade," should read --trade--.
Line 52, "and," should read --and--.
Lines 61-62, "oetacalcium" should read --octacalcium--.

Column 25,
Line 52, "of" should read --or--.

Column 26,
Line 16, "made" should read --made,--.
Line 18, "slings;" should read --slings,--.

Line 42, "aerylate-ethylenepxide:acrylate:acrylic" should read --acrylate-ethyleneoxide:acrylate:acrylic--.
Line 55, "added;" should read --added,--.
Line 64, "hot" should read --not--.

Column 27,
Line 45, "ATGC" should read --ATCC--.
Line 62, "enhancer" should read --enhancer.--.

Column 28,
Line 37, "A4" should read --A 4--.
Line 66, "arc" should read --are--.

Column 29,
In Table 2, under heading "PLA" second item "40600" should read --4060D--.
Line 33, "Adrich" should read --Aldrich--.
Line 47, "initiating," should read --initiating--.
Lines 57-58, "Configurations" should read --configurations--.
Line 59, "sections:were:" should read --sections were--.
Line 67, "fate" should read --rate--.

Column 31,
Line 5, "(C3)," should read --(C3)--.
Line 7, "of" should read --or--.
Line 47, "ah" should read --an--.

Column 32,
Lines 23-24, "*Staphtyococcus*" should read --*Staphylococcus*--.
Line 32, "bottle;" should read --bottle.--.
Line 44, "(CPU's)" should read --(CFU's)--.

Column 33,
Line 21, "method:" should read --method.--.
Line 28, "(CPU's)" should read --(CFU's)--.
Line 42, "*Staphlyococcus*" should read --*Staphylococcus*--.
Line 58, "usinig" should read --using--.

Column 34,
Line 4, "*Staphlyococcus*" should read --*Staphylococcus*--.
Line 15, "*Staphlyococcus*" should read --*Staphylococcus*--.
Line 40, "*Staphlyococcus*" should read --*Staphylococcus*--.

Line 63, "inonlaurate" should read --monolaurate--.

Column 35,
Line 6, "Second" should read --second--.
Line 26, "(PGL," should read --(PCL,--.
Line 54, "(Used" should read --(used--.
Line 56, "protocol)" should read --protocol).--.

Column 36,
Line 6, "of" should read --or--.
Line 17, "Culture" should read --culture--.

Column 37,
Line 8, "*Staphlyococcus*" should read --*Staphylococcus*--.
Line 50, "*Staphlyococcus*" should read --*Staphylococcus*--.
Line 50, "*Pseudodnonas*" should read --*Pseudomonas*--.

In the Claims

Column 38,
Claim 1, Line 61, "acids," should read --acid,--.

Column 40,
Claim 19, Line 67, "aralky" should read --aralkyl--.

Column 44,
Claim 35, Line 6, "foams" should read --foams,--.
Claim 35, Line 7, "materials" should read --materials,--.